US010307371B2

(12) United States Patent
Armer et al.

(10) Patent No.: US 10,307,371 B2
(45) **Date of Patent: *Jun. 4, 2019**

(54) RAPAMYCIN FOR THE TREATMENT OF LYMPHANGIOLEIOMYOMATOSIS

(71) Applicant: AI Therapeutics, Inc., Guilford, CT (US)

(72) Inventors: Thomas Armer, Palo Alto, CA (US); Lawrence S. Melvin, Jr., Niwot, CO (US); Jonathan M. Rothberg, Guilford, CT (US); Henri Lichenstein, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/803,005

(22) Filed: Nov. 3, 2017

(65) Prior Publication Data

US 2018/0200184 A1 Jul. 19, 2018

Related U.S. Application Data

(63) Continuation-in-part of application No. 14/618,621, filed on Feb. 10, 2015, now abandoned.

(60) Provisional application No. 62/060,970, filed on Oct. 7, 2014, provisional application No. 61/938,282, filed on Feb. 11, 2014.

(51) Int. Cl.

| | |
|---|---|
| ***A61K 9/00*** | (2006.01) |
| ***A61K 9/14*** | (2006.01) |
| ***A61K 47/26*** | (2006.01) |
| ***A61P 11/00*** | (2006.01) |
| ***A61K 31/436*** | (2006.01) |

(52) U.S. Cl.

CPC ............ *A61K 9/0075* (2013.01); *A61K 9/145* (2013.01); *A61K 31/436* (2013.01); *A61P 11/00* (2018.01); *A61K 47/26* (2013.01)

(58) Field of Classification Search

None

See application file for complete search history.

(56) References Cited

U.S. PATENT DOCUMENTS

| | | | | |
|---|---|---|---|---|
| 2,517,482 | A | 8/1950 | Hall | |
| 3,929,992 | A | 12/1975 | Sehgal et al. | |
| 5,080,899 | A | 1/1992 | Sturm et al. | |
| 5,478,578 | A * | 12/1995 | Arnold ................. | A61K 9/0075 424/489 |
| 5,635,161 | A | 6/1997 | Adjei et al. | |
| 5,989,591 | A | 11/1999 | Nagi | |
| 6,258,823 | B1 | 7/2001 | Holt et al. | |
| 6,384,046 | B1 | 5/2002 | Schuler et al. | |
| 6,419,900 | B2 | 7/2002 | Placke et al. | |
| 6,419,901 | B2 | 7/2002 | Placke et al. | |
| 6,451,784 | B1 | 9/2002 | Placke et al. | |
| 6,793,912 | B2 | 9/2004 | Pilkiewicz et al. | |
| 7,288,243 | B2 | 10/2007 | Knight et al. | |
| 8,053,444 | B2 | 11/2011 | Reven et al. | |
| 2003/0059375 | A1 | 3/2003 | Perez-Soler et al. | |
| 2004/0018228 | A1 | 1/2004 | Fischell et al. | |
| 2004/0039047 | A1 | 2/2004 | Zamoyski | |
| 2005/0070567 | A1 | 3/2005 | Guan | |
| 2005/0119330 | A1 * | 6/2005 | Kao ..................... | A61K 31/255 514/423 |
| 2006/0210638 | A1 | 9/2006 | Liversidge et al. | |
| 2007/0142422 | A1 | 6/2007 | Rubino et al. | |
| 2008/0008662 | A1 | 1/2008 | Knight et al. | |
| 2008/0127972 | A1 | 6/2008 | Morton | |
| 2010/0166869 | A1 | 7/2010 | Desai et al. | |
| 2010/0189878 | A1 | 7/2010 | Samburski et al. | |
| 2010/0305150 | A1 | 12/2010 | Berg et al. | |
| 2010/0316724 | A1 | 12/2010 | Whitfield et al. | |
| 2012/0077786 | A1 | 3/2012 | Byron et al. | |
| 2013/0004436 | A1 | 1/2013 | Lehrer | |
| 2013/0203717 | A1 | 8/2013 | Gil et al. | |
| 2015/0265582 | A1 | 9/2015 | Armer et al. | |
| 2016/0235668 | A1 | 8/2016 | Lichenstein et al. | |

FOREIGN PATENT DOCUMENTS

| | | | |
|---|---|---|---|
| WO | WO-97/03654 | A2 | 2/1997 |
| WO | WO-97/03654 | A3 | 2/1997 |
| WO | WO-2006/023627 | A1 | 3/2006 |
| WO | WO-2006/039237 | A1 | 4/2006 |
| WO | WO-2006/094507 | A1 | 9/2006 |
| WO | WO-2007/088034 | A2 | 8/2007 |
| WO | WO-2007/088034 | A3 | 8/2007 |
| WO | WO-2010/130982 | A2 | 11/2010 |
| WO | WO-2010/130982 | A3 | 11/2010 |

(Continued)

OTHER PUBLICATIONS

McCormack et al., "Efficacy and Safety of Sirolimus in Lymphangioleiomyomatosis", The New England Journal of Medicine, 364(17) , 2011, pp. 1595-1606. (Year: 2011).*

Ando, Katsutoshi et al., "The efficacy and safety of low-dose sirolinrius for treatment of lymphangioleiomyomatoisis," Respiratory Investigation, vol. 51:175-183 (2013).

Aparicio, Guadalupe et al., "Comprehensive lung injury pathology induced by mTOR inhibitors," Clin. Transl. Oncol., 11:499-510 (2009).

Bissler, John J. et al., "Sirolimus for Angiomyolipoma in Tuberous Sclerosis Complex or Lymphangioleiomyomatosis," The New England Journal of Medicine, vol. 358:140-151 (2008).

(Continued)

*Primary Examiner* — Melissa L Fisher

(74) *Attorney, Agent, or Firm* — Muriel Liberto, Esq.; Mintz Levin Cohn Ferris Glovsky and Popeo, P.C.

(57) ABSTRACT

The present invention relates to methods and compositions for treating lymphangioleiomyomatosis in a human subject in need of such treatment. The methods comprise administering to the subject via inhalation an aerosol composition comprising rapamycin or a prodrug or derivative (including analog) thereof.

7 Claims, 8 Drawing Sheets

(56) References Cited

FOREIGN PATENT DOCUMENTS

| | | | |
|---|---|---|---|
| WO | WO-2011/163600 | A2 | 1/2011 |
| WO | WO-2011/163600 | A3 | 1/2011 |
| WO | WO-2015/054280 | A1 | 4/2015 |
| WO | WO-2015/123219 | A1 | 8/2015 |
| WO | WO-2015/154084 | A1 | 10/2015 |

OTHER PUBLICATIONS

Carvalho, S.R. et al. (Sep. 2014, e-published May 22, 2014). "Characterization and pharmacokinetic analysis of crystalline versus amorphous rapamycin dry powder via pulmonary administration in rats," *Eur J Pharm Bipharm* 88(1):136-147.

Chhajed, Prashant N. et al., "Patterns of Pulmonary Complications Associated with Sirolimus," Respiration, vol. 73:367-374 (2006).

Chougule, Mahavir et al., "Nano-liposomal dry powder inhaler of tacrolimus: Preparation, characterization, and pulmonary pharmacokinetics," International Journal of Nanomedicine, vol. 2(4):675-688 (2007).

Crowe, Andrew et al., "Absorption and Intestinal Metabolism of SDZ-RAD and Rapamycin in Rats," Drug Metabolism and Disposition, vol. 27(5):627-632 (1999).

Davies, D. Mark et al., "Sirolimus Therapy for Angiomyolipoma in Tuberous Sclerosis and Sporadic Lymphangioleiomyomatosis: A Phase 2 Trial," Clin. Cancer Res., vol. 17(12):4071-4081 (2011).

Dr. Reddy's Labs Ltd., "Sirolimus (sirolimus)," retrieved online at: http://fdazilla.com/drugs/application/201578, 2 pages (2015).

European Pharmacopeia, "Feb. 9, 2018. Preparations for Inhalation: Aerodynamic Assessment of Fine Particles," retrieved online at: http://lib.njutcm.edu.cn/yaodian/ep/EP501E/02_methods_ofanalysis/2.9.pharmaceutical_technical_procedures/2.9.18.°/020Preparatione/020for%20inhalation°/020°/020aerodynami0/0 20assessment%20oP/020fine%20particles/2.9.18.pdf, Supplemental edition 5.1, pp. 2799-2811 (2005).

European Pharmacopeia, Chapters 601 and 905, 46 page, retrieved online at: http://www.uspbpep.com/usp32/pub/data/ v32270/usp32nf27s0_c601_html and http://www.uspbpep_com/usp32/pub/data/v32270/usp32nf27s0_c905.html (2015).

FDA, Clinical Review of NDA 22088-s014, retrieved online at: http://www.fda.gov/downloads/Drugs/DevelopmentApprovalProcess/DevelopmentResources/UCM307046.pdf, 49 pages (2009).

Hammes, Stephen R. et al., "Targeted Approaches Toward Understanding and Treating Pulmonary Lymphangioleiomyomatosis (LAM)," Norm_ Cancer, vol. 4(2):70-77 (2013).

Hashemi-Sadraei, N. et al., "Sirolimus-associated diffuse alveolar hemorrhage in a renal transplant recipient on long-term anticoagulation," Clinical Nephrology, vol. 68:238-244 (2007).

Iacovelli, Roberto et al., "Incidence and risk of pulmonary toxicity in patients treated with mTOR inhibitors for malignancy. A meta-analysis of published trials," Acta Oncologica, vol. 51:873-879 (2012).

International Search Report dated Jan. 13, 2015, for PCT Application No. PCT/US2014/059529, filed Oct. 7, 2014, 3 pages.

International Search Report dated May 18, 2015, for PCT Application No. PCT/US2015/015266, filed Feb. 10, 2015, 5 pages.

Johnson, S.R. et al., "Survival and disease progression in UK patients with lymphangioleiomyomatosis," Thorax, vol. 59:800-803 (2004).

Lopez, P. et al. (2014, e-published Dec. 18, 2014). "Interstitial Lung Disease Associated with mTOR Inhibitors in Solid Organ Transplant Recipients: Results from a Large Phase III Clinical Trial Program of Everolimus and Review of the Literature," *J Transplant*, 13 pages.

Louey et al. "Influence of physico-chemical carrier properties on the in vitro aerosol deposition from interactive mixtures", International Journal of Pharmaceutics, 252(1-2), 2003, pp. 87-98.

McCormack, Francis X. et al., "Efficacy and Safety of Sirolimus in Lymphangioleiomyomatosis," The New England Journal of Medicine, 364(17):1595-1606 (2011).

Napoli, Kimberly L. et al., "Distribution of Sirolimus in Rat Tissue," Clinical Biochemistry, vol. 30(2):135-142 (1997).

Neurohr et al. Is sirolimus a therapeutic option for patients with progressive pulmonary lymphangioleiomyomatosis? Respiratory Research 12(66): 1-7, 2011.

Nishimura, Toshihiko et al., "40-0-(2-Hydroxyethyl)-rapamycin Attenuates Pulmonary Arterial Hypertension and Neointimal Formation in Rats," Am. J. Respir. Crit. Care Med., vol. 163:498-502 (2001).

Nocera, A. et al., "Sirolimus Therapy in Liver Transplant Patients: An Initial Experience at a Single Center," Transplantation Proceedings, vol. 40:1950-1952 (2008).

Pedroso, Sofia L. et al., "Pulmonary alveolar proteinosis—a rare pulmonary toxicity of sirolimus," Transplant International, vol. 20:291-296 (2006).

Perez, M.J. et al., "Interstitial Pneumonitis Associated With Sirolimus in Liver Transplantation: A Case Report," Transplantation Proceedings, vol. 39:3498-3499 (2007).

Rao, G.V.S. et al., "Efficacy of a Technique for Exposing the Mouse Lung to Particles Aspirated from the Larynx," Journal of Toxicology and Environmental Health, Part A, vol. 66:1441-1452 (2003).

Ussavarungsi, K. et al. (Nov. 7, 2012). "Sirolimus induced granulomatous interstitial pneumonitis," *Respir Med Case Rep* 7:8-11.

Vahid, Bobbak et al., "Pulmonary Complications of Novel Antineoplastic Agents for Solid Tumors," Chest, vol. 133:528-538 (2008).

Wu, K. et al., "Nonlinear Population Pharmacokinetics of Sirolimus in Patients With Advanced Cancer," CTP: Pharmacometrics & Systems Pharmacology, vol. 1:e17, doi:10.1038/psp.2012.18, 6 pages (2012).

Written Opinion dated Jan. 13, 2015, for PCT Application No. PCT/US2014/059529, filed Oct. 7, 2014, 4 pages.

Written Opinion dated May 18, 2015, for PCT Application No. PCT/US2015/015266, filed Feb. 10, 2015, 6 pages.

Yanez, Jaime A. et al., "Pharmacometrics and delivery of novel nanoformulated PEG-b-poly(epsilon-caprolactone) micelles of rapamycin," Cancer Chemother Pharmacol., vol. 61(1):133-144 (2008).

Yi, Dandan et al., "Inhalation Adjuvant Therapy for Lung Cancer," Journal of Aerosol Medicine and Pulmonary Drug Delivery, vol. 23(4):181-187 (2010).

Gupta, A. et al. (Apr. 7, 2014, e-published Feb. 24, 2014). "Inhalable particles containing rapamycin for induction of autophagy in macrophages infected with *Mycobacterium tuberculosis*," Mol Pharm 11(4):1201-1207.

* cited by examiner

| T-Test P value | OPA-Vehicle (72 hours) | OPA-Rapamycin (1 hour) | Oral Gavage-Rapamycin (1 hour) | OPA-Rapamycin (72 hours) |
|---|---|---|---|---|
| 0.00788 | x | x | | |
| 0.012025 | x | | x | |
| 0.19463 | x | | | x |

RAPAMYCIN FOR THE TREATMENT OF LYMPHANGIOLEIOMYOMATOSIS

CROSS REFERENCE TO RELATED APPLICATION

The present application is a Continuation-in-Part Application of U.S. patent application Ser. No. 14/618,621, filed Feb. 10, 2015, which claims the benefit of priority under 35 U.S.C. § 119(e) to U.S. Provisional Application No. 62/060,970 filed Oct. 7, 2014 and U.S. Provisional Application No. 61/938,282 filed Feb. 11, 2014, each of which is incorporated herein by reference in its entirety.

FIELD OF THE INVENTION

The present invention relates to methods and pharmaceutical compositions comprising rapamycin for pulmonary delivery, preferably by inhalation, for the prophylaxis and treatment of lymphangioleiomyomatosis.

BACKGROUND OF THE INVENTION

Lymphangioleiomyomatosis (LAM) is a multisystem disease affecting 30-40% of women with tuberous sclerosis complex (TSC), an often-fatal disease which is characterized by the widespread proliferation of abnormal smooth muscle-like cells that grow aberrantly in the lung. The proliferation of these cells (referred to as LAM cells) leads to the formation of cysts in the lungs and fluid-filled cystic structures in the axial lymphatics (referred to as lymphangioleiomyomas). The result is progressive cystic destruction of the lung parenchyma, obstruction of lymphatics, airways, and progressive respiratory failure. In addition, LAM cells can form tumors. These are generally slow growing hamartomas referred to as angiomyolipomas. Renal angiomyolipomas can lead to renal failure in LAM patients. The abnormal proliferation of LAM cells is caused at least in part by an inactivating mutation in one of the tuberous sclerosis complex tumor suppressor genes, TSC1 or TSC2. The TSC genes are negative regulators of the mammalian target of rapamycin (mTOR). The mTOR pathway is an important control point for cell growth, metabolism, and cell survival. As a consequence of the inactivation of TSC genes, LAM cells show constitutive activation of mTOR and many other kinases in the mTOR pathway including Akt, and S6K.

LAM generally occurs in women of child-bearing age although it may also occur in men. While it is most prevalent in women having TSC, it can also occur in persons who do not have clinical manifestations of TSC, as well as those who do not have germline mutations in the TSC1 or TSC2 tumor suppressor genes. These cases are referred to as sporadic LAM. Thus, LAM can occur as a sporadic, non-heritable form as well as in association with tuberous sclerosis complex.

Although LAM can progress slowly, it ultimately leads to respiratory failure and death. Ten years after the onset of symptoms 55% of patients are breathless, 20% are on oxygen and 10% are deceased. See e.g., Johnson et al. 2004 *Thorax*. Survival and disease progression in UK patients with lymphangioleiomyomatosis. There is no currently approved drug for the treatment or prophylaxis of LAM. The primary treatment options include the off-label use of oral rapamycin (sirolimus, which is FDA approved for the prophylaxis of organ rejection and renal transplantation, see below), or off-label use of oral everolimus.

Rapamycin is a macrocyclic triene antibiotic produced by *Streptomyces hygroscopicus*. See e.g., U.S. Pat. No. 3,929,992. Rapamycin is an inhibitor of mTOR. The immunosuppressive and anti-inflammatory properties of rapamycin initially indicated its use in the transplantation field and in the treatment of autoimmune diseases. For example, it was shown to prevent the formation of humoral (IgE-like) antibodies in response to an albumin allergic challenge, to inhibit murine T-cell activation, and to prolong survival time of organ grafts in histoincompatable rodents. In rodent models of autoimmune disease, it suppresses immune-mediated events associated with systemic lupus erythematosus, collagen-induced arthritis, autoimmune type I diabetes, autoimmune myocarditis, experimental allergic encephalomyelitis, graft-versus-host disease, and autoimmune uveoretinitis.

Rapamycin is also referred to by its generic drug name, sirolimus (see for example, ANDA #201578, by Dr. Reddys Labs Ltd., approved May 28, 2013). Sirolimus is FDA approved and marketed in the United States for the prophylaxis of organ rejection and renal transplantation under the trade name RAPAMUNE by Wyeth (Pfizer). It is in the form of an oral solution (1 mg/ml) or tablet (multiple strengths). Wyeth (Pfizer) also markets a derivative by the tradename TORISEL (temsirolimus) for the treatment of advanced renal cell carcinoma, which is administered intravenously. Temsirolimus is a water-soluble prodrug of sirolimus. Cordis, a division of Johnson & Johnson, markets a sirolimus-eluting coronary stent under the tradename CYPHER. In this context, the antiproliferative effects of sirolimus prevent restenosis in coronary arteries following balloon angioplasty. US 2010/0305150 to Berg et al. (Novartis) describes rapamycin derivatives for treating and preventing neurocutaneous disorders, such as those mediated by TSC including tuberous sclerosis, as well as those mediated by neurofibromatosis type 1 (NF-1). Rapamycin and its derivatives are further described in Nishimura, T. et al. (2001) *Am. J. Respir. Crit. Care Med.* 163:498-502 and in U.S. Pat. Nos. 6,384,046 and 6,258,823.

Rapamycin use in its clinically approved context has several known adverse effects including lung toxicity (the RAPAMUNE label warns that it is not indicated for lung transplant patients), increased cancer risk, and diabetes-like symptoms. Rapamycin is associated with the occurrence of pulmonary toxicity, usually in the form of interstitial pneumonitis, but pulmonary alveolar proteinosis has also been documented. See for example, Nocera et al., Sirolimus Therapy in Liver Transplant Patients: An Initial Experience at a Single Center, *Transplantation Proceedings* (2008), 40(6), 1950-1952; Perez et al., Interstitial Pneumonitis Associated With Sirolimus in Liver Transplantation: A Case Report, *Transplantation Proceedings* (2007), 39(10), 3498-3499; Hashemi-Sadraei et al., Sirolimus-associated diffuse alveolar hemorrhage in a renal transplant recipient on long-term anticoagulation, *Clinical Nephrology* (2007), 68(4), 238-244; Pedroso et al., Pulmonary alveolar proteinosis—a rare pulmonary toxicity of sirolimus, *Transplant International* (2007), 20(3), 291-296. The cause of rapamycin-induced pulmonary toxicity is not known.

Severe respiratory adverse events have also been associated with sirolimus use as an anti-cancer therapy under chronic administration resulting in circulating blood concentrations greater than 1 nanogram/mL range. For example, the lung toxicity of the sirolimus prodrug, temsirolimus, was documented in a 2009 report noting that "interstitial lung disease is a rare side effect of temsirolimus treatment in renal cancer patients". Aparicio et al., *Clinical & Translational*

*Oncology* (2009), 11(8), 499-510; Vahid et al., Pulmonary complications of novel antineoplastic agents for solid tumors, *Chest* (2008) 133:528-538. In addition, a 2012 meta-analysis concluded that 10% of cancer patients administered temsirolimus or everolimus may experience mild grade toxicity with a worsening of quality of life and, in some case, interruption of therapy. See Iacovelli et al., Incidence and risk of pulmonary toxicity in patients treated with mTOR inhibitors for malignancy. A meta-analysis of published trials, *Acta oncologica* (2012), 51(7), 873-879. Furthermore, safety pharmacology studies performed in rats with temsirolimus showed reductions in respiratory rate as well as alveolar macrophage infiltration and inflammation in the lungs (see Pharmacology Review for temsirolimus NDA 22088 available from the US FDA website). These adverse effects were observed under conditions of relatively high concentrations of the drug in the circulating blood volume as a result of systemic administration.

Despite its potential for toxicity to the lung, orally administered rapamycin has shown preliminary promise as a potential LAM therapy. See *New Eng. J. Medicine* 364: 1595-1606 (2011) and review by Hammes and Krymskaya, *Horn. Cancer* 4(2):70-7 (2013); see also Ando et al. *Respir Investig.* 51(3):175-8 (2013) "The efficacy and safety of low-dose sirolimus for treatment of lymphangioleiomyomatosis". But the clinical evidence also indicates the limitations of rapamycin in this context and the need for improved therapies and therapeutic regimens for the treatment of LAM. The primary limitations of rapamycin are the need to use the drug chronically, and most importantly, that rapamycin is associated with other adverse events (in addition to potential lung toxicities). For example, in a 24 month non-randomized open label trial completed in 20 patients, sirolimus administered orally was tested for its ability to reduce angiomyolipomas, which are slow growing hamartomas that can lead to renal failure in patients with TSC or sporadic LAM. Bissler et al. (2008) Sirolimus for angiomyolipoma in tuberous sclerosis complex or lymphangioleiomyomatosis. *N Engl J Med* 358(2):140-151. In that study, angiomyolipomas regressed "somewhat" during the treatment period but tended to increase after therapy stopped. Serious adverse events associated with sirolimus included diarrhea, pneumonia, pyelonephritis, cellulitis (from an animal bite), stomatitis, and hemorrhage of a renal angiomyolipoma. Dosing was based on the serum target levels that would prevent rejection in renal transplant patients and ranged from 1 to 15 ng/ml (blood sirolimus level). In another similar study (phase 2, non-randomized open label trial) 16 patients with TSC or sporadic LAM were treated with oral sirolimus for up to 2 years. Davies et al (2011) Sirolimus therapy for angiomyolipoma in tuberous sclerosis and sporadic lymphangioleiomyomatosis: a phase 2 trial. *Clin Cancer Res* 17(12):4071-4081. In that study, steady state blood levels of sirolimus were 3-10 ng/ml with more than half of the patients maintained on maintenance levels of 3-6 ng/ml. Sirolimus treatment showed sustained regression of renal angiomyolipomas. However, while tumor response was maintained with continuation of therapy, little further shrinkage occurred during the second year of treatment. Adverse events associated with sirolimus included oral mucositis, respiratory infections, and proteinuria. In another study of 10 LAM patients with documented progression, sirolimus was discontinued in 3 patients because of serious recurrent lower respiratory tract infection or sirolimus-induced pneumonitis. *Neurohr* et al., Is sirolimus a therapeutic option for patients with progressive pulmonary lymphangioleiomyomatosis? *Respiratory Research* (2011), 12:66. That study concluded that "sirolimus might be considered as a therapeutic option in rapidly declining LAM patients" but noted that its "administration may be associated with severe respiratory adverse events requiring treatment cessation in some patients" and that "discontinuation of sirolimus is mandatory prior to lung transplantation." Finally, a 12 month randomized, double-blind 89 patient clinical trial was conducted with 46 patients having LAM, followed by a 12 month observation period. McCormack et al (2011) Efficacy and safety of sirolimus in lymphangioleiomyomatosis. *N Engl J Med* 364:1595-1606. Patients were maintained at sirolimus blood levels of 5-15 ng/ml. In this study, sirolimus treatment stabilized lung function, reduced serum VEGF-D levels, and was associated with a reduction in symptoms and improved quality of life. But stabilization of lung function required continuous treatment. Importantly, all of these clinical studies utilized oral formulations of sirolimus. This is because an aerosol formulation of rapamycin for delivery directly to the lungs was considered highly unlikely to succeed in view of rapamycin's well-known lung toxicity, as exemplified by the articles cited above.

A U.S. patent application by Lehrer published in 2013 reflects the view that "[r]apamycin (sirolimus) cannot be safely inhaled because of its well-documented lung toxicity, interstitial pneumonitis". See US 20130004436, citing Chhajed et al. (2006) 73:367-374. The Lehrer patent application is directed to compositions and methods for treating and preventing lung cancer and lymphangioleiomyomatosis. Although some earlier publications, such as U.S. Pat. No. 5,080,899 to Sturm et al. (filed February 1991) and U.S. Pat. No. 5,635,161 (filed June 1995), contain some generic description of rapamycin formulated for delivery by inhalation, such generic descriptions were unsupported by any evidence and came before the many reported incidences of rapamycin-induced lung toxicity that appeared following its more widespread adoption as an immunosuppressant in the transplantation context and as an inhibitor of cellular proliferation in the anti-cancer context, as evidenced by the reports discussed above.

WO 2011/163600 describes an aerosol formulation of tacrolimus, which like rapamycin is a macrolide lactone. But tacrolimus is a distinct chemical entity from sirolimus and the molecular target of tacrolimus is calcineurin, not mTOR, and unlike rapamycin, tacrolimus did not show lung toxicity and in fact is indicated for preventing rejection following lung transplantations.

In view of the wide-spread recognition of the potential for rapamycin-induced lung toxicity, a pharmaceutical composition comprising rapamycin for pulmonary delivery in the treatment of LAM was not considered to be a viable therapeutic option in humans.

Delivery of drugs to the lung by way of inhalation is an important means of treating a variety of conditions, including such common local conditions as cystic fibrosis, pneumonia, bronchial asthma and chronic obstructive pulmonary disease, some systemic conditions, including hormone replacement, pain management, immune deficiency, erythropoiesis, diabetes, lung cancer, etc. See review by Yi et al. *J. Aerosol Med. Pulm. Drug Deliv.* 23:181-7 (2010). Agents indicated for treatment of lung cancer by inhalation include cisplatin, carboplatin, taxanes, and anthracyclines. See e.g., U.S. Pat. Nos. 6,419,900; 6,419,901; 6,451,784; 6,793,912; and U.S. Patent Application Publication Nos. US 2003/0059375 and US 2004/0039047. In addition, doxorubicin and temozolomide administered by inhalation have been suggested for treating lung metastases. See e.g., U.S. Pat. No. 7,288,243 and U.S. Patent Application Publication No. 2008/0008662.

SUMMARY OF THE INVENTION

Figure 1:
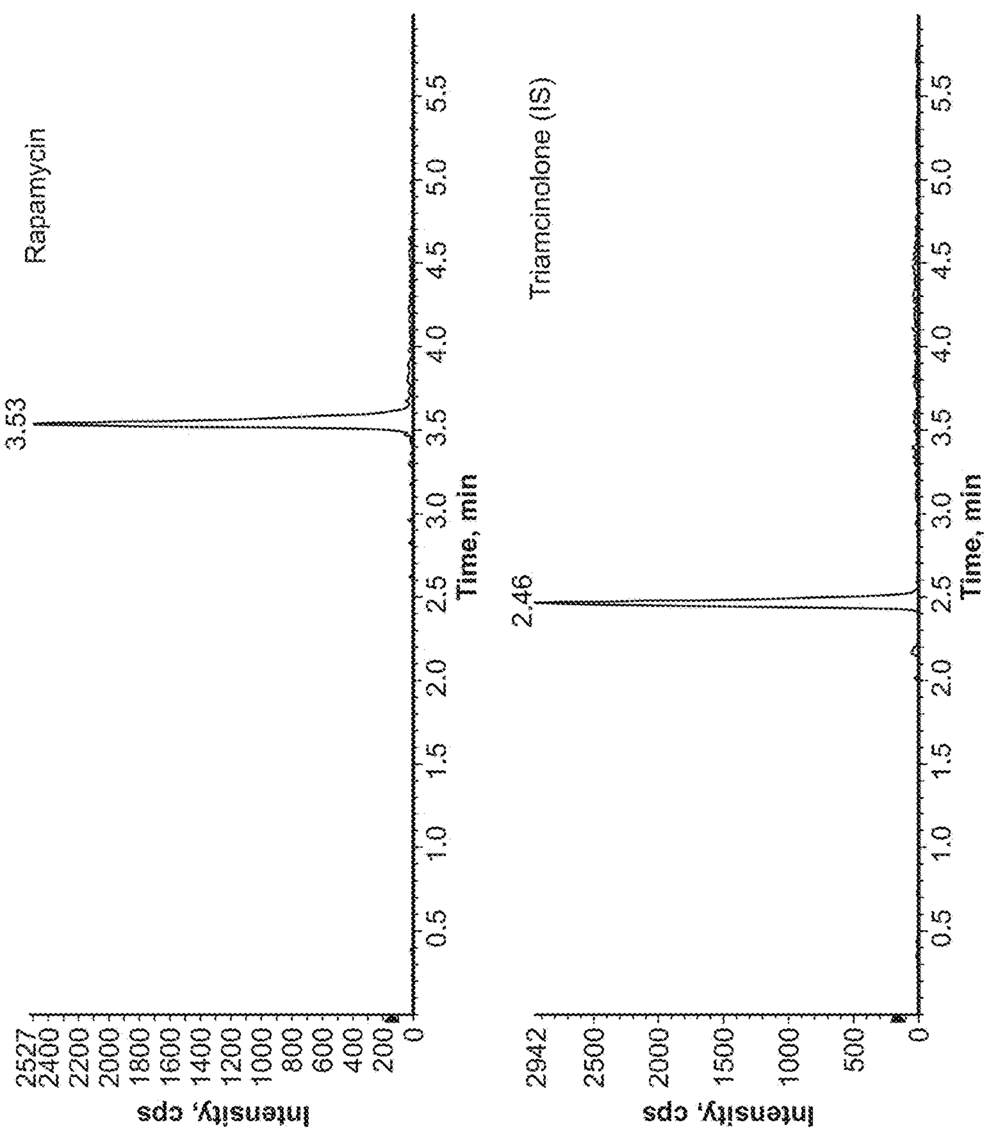
FIG. 1: LC-MS/MS Chromatogram of 10.6 ng/mL Rapamycin (top) and Internal Standard (bottom) in Mouse Blood.

The present invention is based, in part, upon the discovery of surprising pharmacokinetics of rapamycin when it was delivered directly to the lungs in animal studies. The results discussed infra show that delivery of rapamycin to the lungs by inhalation produced markedly higher concentrations of drug in the lung tissue, amounts that were unexpectedly higher than what was predictable from previous studies, along with significantly higher lung to blood ratios than could be achieved by alternative routes of administration, such as oral or intravenous. The results described here demonstrate that administering rapamycin to the lungs via inhalation advantageously provides for a low dose of rapamycin required to achieve therapeutically effective amounts of drug in the lung combined with extremely low systemic exposure to the drug, resulting in markedly improved therapeutic index for rapamycin.

In one aspect, the present invention addresses the need for pharmaceutical formulations of rapamycin, its prodrugs, derivatives, and analogues, delivered directly to the lungs, preferably by inhalation, in order to provide an effective local treatment and prophylaxis of diseases and disorders of the lungs. In one aspect, the disease or disorder is one potentiated by inappropriate activity of the mTOR signaling pathway. Such localized treatment reduces or eliminates the toxicities and adverse events, including those associated with elevated concentrations of rapamycin in the blood resulting from systemic delivery of the drug.

The present invention provides rapamycin compositions for delivery directly to the lungs. As used herein, the term "rapamycin composition" may refer to rapamycin itself, preferably in the amorphous form described as sirolimus, or a prodrug, or derivative thereof. In one embodiment, a rapamycin composition of the invention provides an amount of rapamycin effective to inhibit mTOR signaling in the lung with low or no toxicity to lung tissue, and concomitant blood levels of rapamycin that are less than about 1 ng/ml. In one embodiment, a rapamycin composition of the invention provides an improved safety profile, as evidenced by a higher therapeutic index, especially with respect to its chronic or prolonged use, compared to other dosage forms of rapamycin, for example oral or intravenous dosage forms.

In one embodiment, the present invention provides compositions and methods for the treatment and prophylaxis of LAM by administering to a subject in need thereof a pharmaceutical aerosol formulation comprising a rapamycin composition in an amount effective to achieve a therapeutic level of the composition in the lungs combined with sub-therapeutic blood levels of the composition. In one embodiment, the subject is a human subject in need of such treatment. The compositions of the invention may be used alone, or in combination with one or more additional therapies or therapeutic regimens for the treatment of LAM. In addition, the compositions provided herein may comprise rapamycin, or a prodrug or derivative thereof, as the sole therapeutic agent in the composition, or the rapamycin may be formulated with one or more additional therapeutic agents in a single dosage form.

In one embodiment, the present invention provides a pharmaceutical aerosol formulation comprising a rapamycin composition in an amount effective to achieve a therapeutic level of the composition in the lungs combined with sub-therapeutic blood levels of the composition. In this context, the term "aerosol formulation" may refer to an aqueous composition, a dry powder composition, or a propellant-based composition, as described in more detail infra. An aerosol formulation may be delivered to a subject in different ways, for example nasally or perorally, e.g., by inhalation. In one embodiment, the therapeutic level is determined 12 or 24 hours after delivery, preferably 24 hours after delivery. In one embodiment, the therapeutic level in the lung is sustained for at least 24 hours after delivery. In one embodiment, the lung to blood concentration ratio of the composition 24 hours after delivery is at least 100, at least 250, or at least 500. In one embodiment, the lung to blood concentration ratio of the composition 24 hours after delivery is from about 100 to 250, 250 to 500, 500 to 750, or 750 to 1000. In one embodiment, the lung to blood concentration ratio of the composition 24 hours after delivery is at least 5, at least 10, at least 20, at least 30, at least 50, at least 60, at least 70, at least 80, or at least 100.

In one embodiment, the amount of the rapamycin composition in the aerosol formulation is from 5 to 500 micrograms, from 10 to 250 micrograms, from 15 to 150 micrograms, or from 20 to 100 micrograms. In one embodiment, the amount of the rapamycin composition in the aerosol formulation is 20 micrograms. In one embodiment, the amount of the rapamycin composition in the aerosol formulation is 40 micrograms. In one embodiment, the amount of the rapamycin composition in the aerosol formulation is 50 micrograms. In one embodiment, the amount of the rapamycin composition in the aerosol formulation is 100 micrograms. In one embodiment, the amount of the rapamycin composition in the aerosol formulation is 125 micrograms. In one embodiment, the amount of the rapamycin composition in the aerosol formulation is 250 micrograms.

In one embodiment, the rapamycin composition is sirolimus. In one embodiment, the rapamycin composition is selected from the group consisting of everolimus, temsirolimus, ridaforolimus, umirolimus, and zotarolimus.

In one embodiment, the aerosol formulation is a dry powder composition suitable for delivery by inhalation. In one embodiment, the dry powder comprises the rapamycin composition in the form of microparticles, particles of a carrier, and one or more optional excipients. In one embodiment, the microparticles consist of particles of drug having mean diameters from about 0.1 to 10 microns or from about 1 to 5 microns. In one embodiment, the particles have a mean diameter of about 1.5 to 4 microns, about 1.5 to 3.5 microns, or about 2 to 3 microns. The carrier may be selected from the group consisting of arabinose, glucose, fructose, ribose, mannose, sucrose, trehalose, lactose, maltose, starches, dextran, mannitol, lysine, leucine, isoleucine, dipalmitylphosphatidylcholine, lecithin, polylactic acid, poly (lactic-co-glutamic) acid, and xylitol, and mixtures of any of the foregoing. In one embodiment, the carrier comprises or consists of a blend of two different carriers. The particles of carrier may have diameters ranging from to 200 microns, from 30 to 100 microns, or less than 10 microns. Where the carrier consists of a blend of two different carriers, each carrier consists of particles of a different size range, measured as average particle diameter. In one embodiment, the carrier consists of a blend of two different carriers, a first carrier and a second carrier. The first carrier consists of particles having diameters ranging from about 30-100 microns and the second carrier consists of particles having diameters of less than 10 microns. The ratio of the two different carriers is in the range of from 3:97 to 97:3. In one embodiment, the ratio of the two different carriers is in the range of from 97:3 or from 95-98:2-5. In one embodiment, the carrier consists of a blend of two different lactose carriers. The drug to carrier ratio in the powder may be from 0.5% to 2% (w/w). In one embodiment, the drug to carrier ratio in the powder is 1% (w/w).

The amount of the rapamycin composition in the aerosol formulation is from about 0.1% to 20% (w/w) based upon total weight of the composition. In one embodiment, the amount is from about 0.25% to 2% (w/w).

In one embodiment, the one or more optional excipients is present in the composition and is selected from a phospholipid and a metal salt of a fatty acid, and mixtures of the foregoing. In one embodiment, the phospholipid is selected from dipalmitylphosphatidylcholine and lecithin. In one embodiment, the metal salt of a fatty acid is magnesium stearate. In one embodiment, the excipient or excipients is coated on the carrier particles in a weight ratio of excipient to large carrier particle ranging from 0.01 to 0.5%.

In one embodiment, the amount of the rapamycin composition in the aerosol formulation is an amount effective to inhibit the biological activity of mTORC1. In one embodiment, the amount is an amount effective to inhibit the phosphorylation of the S6K protein.

In one embodiment, the amount of the rapamycin composition in the aerosol formulation is an amount effective to achieve a respirable dose of from 5 to 500 micrograms delivered to the lung. In one embodiment, the respirable dose is about 5, about 20, about 50, about 100 or about 250 micrograms. In one embodiment, the respirable dose is about 20 micrograms, about 50 micrograms, or about 100 micrograms. In one embodiment, the amount is an amount effective to produce a concentration of the rapamycin composition in the lung tissue of from 1 ng/g to 1 microgram (ug)/g. In one embodiment, the concentration of the rapamycin composition in the lung tissue is from about 5 to 30 ng/g. In one embodiment, the concentration in the lung tissue is about 5 ng/g, about 10 ng/g, about 15 ng/g, about 20 ng/g, about 25 ng/g, about 30 ng/g, about 50 ng/g, about 60 ng/g, about 100 ng/g, or about 200 ng/g. In accordance with the foregoing embodiments, the concomitant blood trough level of the rapamycin composition is less than 5 ng/ml, less than 2 ng/ml, less than 1 ng/ml, less than 0.5 ng/ml, or less than 0.25 ng/ml. In one embodiment, the blood trough level is less than 1 ng/ml, less than 0.5 ng/ml or less than 0.25 ng/ml.

In one embodiment, the rapamycin composition persists in lung at therapeutic levels of about 1 ng/g, about 5 ng./g, about 10 ng/g, about 15 ng/g, about 20 ng/g, about 25 ng/g, about 50 ng/g, or about 100 ng/g for a period of time after administration, preferably to a human subject, the period of time selected from about 6 to 10 hours, about 6 to 14 hours, about 6 to 24 hours, and about 6 to 72 hours. In one embodiment, the period of time is selected from about 12 hours, about 14 hours, about 24 hours, and about 72 hours.

In one embodiment, the rapamycin composition persists in lung at therapeutic levels of about 5 to 100 ng/g or from about 5 to 30 ng/g for a period of time that is about 12 or 24 hours. In one embodiment, the rapamycin composition persists in lung at therapeutic levels of about 5 ng/g, about 10 ng/g, about 20 ng/g, about 30 ng/g, about 50 ng/g, about 60 ng/g, about 70 ng/g, about 80 ng/g, or about 90 ng/g. In one embodiment, the rapamycin composition persists in lung at therapeutic levels of at least 5 ng/g, at least 20 ng/g, or at least 30 ng/g. In one embodiment, the rapamycin composition persists in lung at therapeutic levels of from about 20 ng/g to about 30 ng/g or from about 50 ng/g to about 80 ng/g.

In one embodiment, the formulation has a fine particle fraction (FPF) greater than 20% with a corresponding fine particle dose (FPD) ranging from 5 micrograms to 2 milligrams, preferably less than 0.5 milligrams, following 1 to 12 months or 1 to 36 months of storage. In one embodiment, the respirable dose, which is the dose delivered to the lung, also referred to as the delivered dose (DD) or emitted dose (ED), ranges from 10 micrograms to 2.5 milligrams, preferably less than 0.5 milligrams. In one embodiment, the delivered dose is from about 20 to 100 micrograms, from about 10 to 25 micrograms or from about 30 to 60 micrograms. In one embodiment, the delivered dose is 20 or 50 micrograms. In one embodiment, the delivered dose is 100 micrograms.

In one embodiment, the respirable dose of the rapamycin composition is about 20 micrograms, the concentration of drug in the lung tissue is from about 5 to 25 ng/g, the Cmax in blood is less than 1.0 ng/ml, or from about 0.50 ng/ml to 1.0 ng/ml, or about 0.50 ng/ml to 0.90 ng/ml, the blood trough concentration of drug at 24 hrs post-dosing is less than about 0.20 ng/ml, and the steady-state concentration of drug in the blood at 14 days post-dosing is less than about 0.90 ng/ml, or less than about 0.80 ng/ml.

In one embodiment, the respirable dose of the rapamycin composition is about 50 micrograms, the concentration of drug in the lung tissue is about 2 to 15 ng/g, the Cmax in blood is less than 2.0 ng/ml, or from about 0.25 ng/ml to 0.1 ng/ml, or about 0.10 ng/ml to 0.5 ng/ml, the blood trough concentration of drug after a single dose, 24 hrs post-dosing is less than about 0.10 ng/ml, and the trough concentration of drug in the blood after 5 days repeated, once-daily, is less than about 1.0 ng/ml, or less than about 0.50 ng/ml.

In one embodiment, the formulation further comprises one or more additional therapeutic agents. The one or more additional therapeutic agents may be selected from an estrogen antagonist (e.g., letrozole, tamoxifen), a statin (e.g., simvastatin), a src inhibitor (e.g., saracatinib), and a VEGF receptor inhibitor (e.g., pazopanib). In one embodiment, the one or more additional therapeutic agents is selected from letrozole, tamoxifen, simvastatin, saracatinib, pazopanib, and imatinib.

In one embodiment, the pharmaceutical aerosol formulation comprising a rapamycin composition as described herein is administered along with at least one additional therapeutic agent as part of a therapeutic regimen or combination therapy. The at least one additional therapeutic agent may be administered by the same or different route of administration from the aerosol formulation. In one embodiment, the at least one additional therapeutic agent is administered orally, for example in the form of an oral dosage form such as a tablet or capsule. The one or more additional therapeutic agents may be selected from an estrogen antagonist (e.g., letrozole, tamoxifen), a statin (e.g., simvastatin), a src inhibitor (e.g., saracatinib), and a VEGF receptor inhibitor (e.g., pazopanib). In one embodiment, the one or more additional therapeutic agents is selected from letrozole, tamoxifen, simvastatin, saracatinib, pazopanib, and imatinib.

In one embodiment, the formulation delivers an amount of the rapamycin composition effective to improve the subject's pulmonary function as measured by forced vital capacity (FVC) and forced expiratory volume (FEV1). In one embodiment, the formulation delivers an amount of the rapamycin composition effective to reduce the size or amount of pleural effusion detectable by radiologic examination.

In one embodiment, the formulation is adapted for once daily administration.

In one embodiment, the formulation is produced by a wet polishing process comprising the steps of preparing an aqueous suspension of drug, subjecting the drug suspension to microfluidization, and spray-drying the resulting particles to form a dry powder.

In one embodiment, the rapamycin composition is sirolimus, the carrier consists of a blend of two different lactose carriers, the first carrier consists of particles having average diameters ranging from about 30-100 microns and the second carrier consists of particles having average diameters of less than 10 microns, the ratio of the two different carriers is about 97:3 to 3:97, and the amount of rapamycin is from 25 to 1400 micrograms.

The invention also provides a unit dosage form for treating LAM comprising an aerosol formulation comprising a rapamycin composition as described herein, wherein the amount of the rapamycin composition is from about 5 to 2500 micrograms, from 20 to 500 micrograms, or from 50 to 250 micrograms. In one embodiment, the amount of the rapamycin composition is from about 50 to 125 micrograms. In one embodiment, the amount of the rapamycin composition is about 40, about 50, about 100, about 125, or about 250 micrograms. In one embodiment, the amount of the rapamycin composition is about 250 micrograms.

In one embodiment, the unit dosage form is a capsule suitable for use in a dry powder inhaler device. In one embodiment, the capsule contains from 1 mg to 100 mg of the powder (total amount, including the rapamycin composition, carrier, and any optional excipients) or from 10 mg or 40 mg of the powder. The capsule may be a gelatin, plastic, or cellulosic capsule, or in the form of a foil/foil or foil/plastic blister suitable for use in a DPI device.

The invention also provides a pharmaceutical package or kit comprising a composition or unit dosage form described herein, and instructions for use.

The invention also provides a dry powder delivery device comprising a reservoir containing a composition or unit dosage form described herein. The reservoir may be an integral chamber within the device, a capsule, or a blister. In one embodiment, the device is selected from Plastiape® RS01 Model 7, Plastiape® RS00 Model 8, XCaps®, Handihaler®, Flowcaps® TwinCaps®, and Aerolizer®. In one embodiment, the device is selected from Plastiape® RS01 Model 7 or Plastiape® RS00 Model 8. In one embodiment, the device is Plastiape® RS00 Model 8.

The invention also provides a method for treating LAM in a human subject in need of such treatment, the method comprising administering to the subject via inhalation a composition or unit dosage form described herein.

DETAILED DESCRIPTION OF THE INVENTION

The present invention provides methods and compositions for the treatment and prophylaxis of LAM in a human subject in need of such treatment. The human subject in need of such treatment is one who has been diagnosed with LAM. In one embodiment, the human subject is a woman. In one embodiment, the human subject is a man. In one embodiment, the human subject has been diagnosed with tuberous sclerosis complex. In one embodiment, the human subject has been diagnosed with sporadic LAM. In one embodiment, the methods comprise administering to the subject via inhalation a composition comprising rapamycin in a suitable carrier, and optionally one or more additives. The term "rapamycin" is used generically throughout this disclosure to refer to rapamycin itself, also referred to as sirolimus, as well as to its prodrugs (such as temsirolimus) and derivatives. Derivatives of rapamycin include compounds that are structurally similar to rapamycin, are in the same chemical class, are rapamycin analogs, or are pharmaceutically acceptable salts of rapamycin or its derivatives. Further description and examples of rapamycin, its prodrugs, and derivatives are provided in the following section.

The compositions described herein are referred to as "aerosol formulations" and are meant to describe aerosolizable compositions suitable for producing respirable particles or droplets containing a rapamycin composition, which as described above refers to rapamycin itself, preferably in the amorphous form described as sirolimus, or a prodrug, or derivative thereof. In one embodiment, the rapamycin composition is selected from sirolimus, everolimus, and temsirolimus. In one embodiment, the rapamycin composition is sirolimus. The aerosol formulations described herein may comprise the rapamycin composition, a carrier, and optionally one or more additives. The aerosol formulations may be in the form of an aqueous solution, a dry powder, or a mixture of one or more pharmaceutically acceptable propellants and a carrier, as described in detail in the section below entitled "Compositions for Inhalation".

The present invention also provides methods for the treatment and prophylaxis of LAM in a human subject in need of such treatment, the methods comprising the step of pulmonary administration of an aerosol formulation of the invention to the subject. In one embodiment, the administered dose of the rapamycin composition is sufficient to achieve therapeutic levels of rapamycin in the lung tissue while maintaining a low blood level, or blood trough level, in the subject. For example, the therapeutic levels of the rapamycin composition may be from about 1 ng/g, about 5 ng./g, about 10 ng/g, about 15 ng/g, about 20 ng/g, about 25 ng/g, about 50 ng/g and the blood trough level is from 0.01 to 0.15 ng/ml, from 0.075 to 0.350 ng/ml, from 0.150 to 0.750 ng/ml, from 0.750 to 1.5 ng/ml, or from 1.5 to 5 ng/ml. In one embodiment, the administered dose is sufficient to achieve a therapeutic level of drug in the lung of from about 5 ng/g to 50 ng/g, or from about 5 ng/g to 20 ng/g and a blood trough level of drug of less than 5 ng/ml, less than 2 ng/ml, less than 1 ng/ml, or less than 0.5 ng/ml. In one embodiment, the lung to blood concentration ratio of the rapamycin composition 24 hours after delivery is at least 100, at least 250, or at least 500. In one embodiment, the lung to blood concentration ratio of the rapamycin composition 24 hours after delivery is from about 100 to 250, 250 to 500, 500 to 750, or 750 to 1000.

Preferably, the aforementioned therapeutic levels are achieved by administering an aerosol formulation described herein once a day. In one embodiment, the total daily dose of the rapamycin composition is in the range of from 5 to 100 micrograms, from 20 to 250 micrograms, from 50 to 500 micrograms (0.05 to 0.5 milligrams), from 250 to 1000 micrograms (0.25 to 1 milligrams) or from 500 to 2000 micrograms (0.5 to 2 milligrams). In one embodiment, the total daily dose is less than 500 micrograms, less than 100 micrograms, less than 50 micrograms, less than 20 micrograms, or less than 10 microgram. In one embodiment, the total daily dose is less than 500 micrograms, less than 250 micrograms, less than 100 micrograms, less than 50 micrograms, or less than 10 micrograms. In one embodiment, the total daily dose administered to the subject is less than 0.5 mg or less than 0.25 mg per day. Further aspects of pulmonary delivery and dosing, including combination therapies, are described in the section below entitled "Pulmonary Administration and Dosing".

The methods and compositions of the invention are effective to treat LAM in a subject in need of such treatment, preferably a human subject. The amount of drug effective to treat LAM (the "effective amount" or "therapeutically effective amount") refers to the amount of drug (e.g., rapamycin) which is sufficient to reduce or ameliorate the progression, severity, and/or duration of LAM or one or more symptoms of LAM, to prevent the advancement of LAM, cause the regression of LAM, or prevent the development or onset of one or more symptoms associated with LAM, or enhance or improve the prophylactic or therapeutic effect(s) of another therapy (e.g., a prophylactic or therapeutic agent) with respect to the severity or onset of one or more symptoms of LAM, or with respect to the development or progression of LAM. In specific embodiments, with respect to the treatment of LAM, a therapeutically effective amount refers to the amount of a therapy (e.g., therapeutic agent) that inhibits or reduces the proliferation of LAM cells, inhibits or reduces the spread of LAM cells (metastasis), or reduces the size of a tumor or improves FVC or FEV1 or reduces the amount of pleural effusion detectable by radiologic examination. In a preferred embodiment, a therapeutically effective amount of a therapy (e.g., a therapeutic agent) reduces the proliferation of LAM cells or the size of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to a control (e.g., phosphate buffered saline ("PBS")). Thus, in the context of the methods of the invention, the terms "treat", "treatment", and "treating" refer to the reduction of the severity, duration, or progression of LAM or one or more symptoms associated with LAM. In specific embodiments, these terms may refer to the inhibition of proliferation or reduction in proliferation of LAM cells, the inhibition or reduction in the spread (metastasis) of LAM cells, or the development or progression of a LAM-associated cancer, or the reduction in the size of a LAM-associated tumor, or the reduction or the involvement of axial lymphatics.

In one embodiment of the methods of the invention, the rapamycin is administered in a dose effective to improve the subject's pulmonary function as measured by forced vital capacity (FVC) and forced expiratory volume (FEV1). In another embodiment, the rapamycin is administered in a dose effective to reduce the size or amount of pleural effusion in the subject that is detectable by radiologic examination. In one embodiment, the rapamycin is administered in a dose effective to improve one or more of the following: functional residual capacity, serum VEGF-D, quality of life and functional performance, 6 minute walk distance, and diffusing capacity of the lung for carbon monoxide. In one embodiment, rapamycin delivered via a pulmonary route achieves blood levels of rapamycin effective to limit the growth of LAM-related tumors in the lungs and at sites distant from the lung. In one embodiment, the efficacy of the administered dose of rapamycin is measured by any one or more of the foregoing.

In certain embodiments, the methods of the invention are effective to manage LAM in a subject having LAM. In this context, the terms "manage", "managing", and "management" refer to the beneficial effects that a subject derives from a therapy which does not result in a cure. In one embodiment, LAM is managed in the subject if its progression is slowed or stopped during treatment with rapamycin according to the methods of the invention. In another embodiment, LAM is managed in the subject if one or more symptoms associated with LAM is ameliorated or stabilized (i.e., the symptom does not worsen during the course of treatment).

In one embodiment, the methods of the invention are directed to subjects who are "non-responsive" or "refractory" to a currently available therapy for LAM. In this context, the terms "non-responsive" and "refractory" refer to the subject's response to therapy as not clinically adequate to relieve one or more symptoms associated with LAM. The terms "subject" and "patient" are used interchangeably in this invention disclosure. The terms refer to an animal, preferably a mammal including a non-primate (e.g., a cow, pig, horse, cat, dog, rat, and mouse) and a primate (e.g., a chimpanzee, a monkey such as a cynomolgous monkey and a human), and more preferably a human. In a preferred embodiment, the subject is a human.

The terms "prevent", "preventing" and "prevention" refer to the prevention of the recurrence, development, progression or onset of one or more symptoms of LAM resulting from the administration of one or more compounds identified in accordance the methods of the invention or the administration of a combination of such a compound and a known therapy for a disease or disorder.

In the context of the pharmaceutical compositions of the invention, a "carrier" refers to, for example, a liquid or solid material such as a solvent, a diluent, stabilizer, adjuvant, excipient, auxiliary agent, propellant, or vehicle with which rapamycin is formulated for delivery. Examples of pharmaceutically acceptable carriers for use in the compositions of the invention include, without limitation, dry powder carriers such as lactose, mannose, amino acids, cyclodextrin, dipalmitylphosphatidylcholine, hydrocarbon and fluorocarbon propellants, compressed gases, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof. Preferably, in the context of the dry powder aerosol formulations of rapamycin, the carrier, if present, is selected from the group consisting of a saccharide and a sugar alcohol. In one embodiment, the carrier, if present, is lactose.

The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. One method for solubilizing poorly water soluble or water insoluble drugs is to form a salt of the drug or to prepare a prodrug that is more soluble itself or that can be used to form a water soluble salt of the prodrug. Methods for forming salts and pharmaceutically acceptable salt forms are known in the art and include, without limitation, salts of acidic or basic groups that may be present in the drug or prodrug of interest. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

In one embodiment, the methods and compositions of the invention utilize a water soluble prodrug or derivative of rapamycin, preferably temsirolimus or related compound. In one embodiment, the methods and compositions of the invention utilize rapamycin (sirolimus).

Rapamycin

Rapamycin is a macrocyclic lactone produced by *Streptomyces hygroscopicus* Its chemical (IUPAC) name is (3S,6R,7E,9R,10R,12R,14S,15E,17E,19E,21S,23S,26R,27R,34aS)-9,10,12,13, -14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethox-y-6,8,12,14,20,26-hexamethyl-23,27-epoxy-3H-pyrido[2,1-c][1,4]oxaazacyclohentriacontine-1,5,11,28,29 (4H,6H,31H)-pentone.

Its molecular formula is $C_{51}H_{79}NO_{13}$ and its molecular weight is 914.172 g/mol. Its structure is shown below.

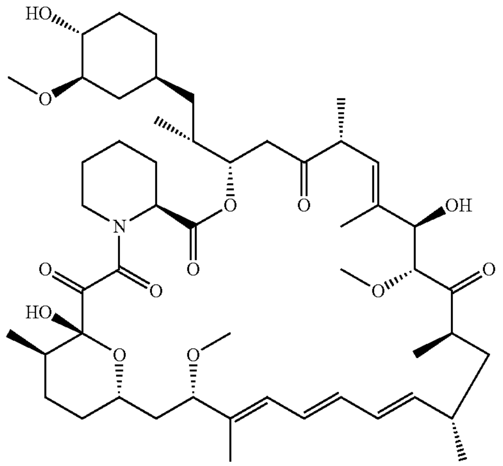 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Rapamycin is a white to off-white powder and is considered insoluble in water, having a very low solubility of only 2.6 μg/ml. It is freely soluble in benzyl alcohol, chloroform, acetone, and acetonitrile. The water insolubility of rapamycin presents special technical problems to its formulation. In the context of its formulation as an oral dosage form, it has been prepared as an oral solution in the form of a solid dispersion (WO 97/03654) and a tablet containing nanosized (less than 400 nm) particles (U.S. Pat. No. 5,989,591). But these procedures suffer from substantial variation in the dissolution of the active and therefore its bioavailability. Another method of formulation utilizes the crystalline powder. According to art-recognized methods, the transformation of the crystalline form of a low solubility drug to its amorphous form can significantly increase its solubility. While this is also true for rapamycin, the amorphous form is extremely chemically unstable. Pharmaceutical dosage forms comprising amorphous rapamycin (sirolimus) are described in WO 06/039237 and WO 06/094507 (modified release formulation comprising sirolimus and glyceryl monostearate at a concentration of 49.25%). An improved stable oral dosage form of rapamycin is described in U.S. Pat. No. 8,053,444. The dosage form employs a fatty acid ester and a polymer (e.g., polyvinylpyrrolidone (PVP), hydroxypropylcellulose (HPC) or hydroxypropylmethylcellulose (HPMC)) in the composition to increase the stability of sirolimus without adversely affecting its release rate. According to U.S. Pat. No. 8,053,444, a fatty acid ester concentration exceeding 10% w/w suppresses the release rate of sirolimus from the formulation and so should be avoided because it can lead to insufficient absorption from the gastrointestinal tract. The preferred concentration of fatty acid ester (glycerol ester) is 1% to 5% or 5% to 9%. In one embodiment, the aerosol rapamycin compositions of the present invention do not contain a fatty acid ester in combination with a polymer. In one embodiment, the aerosol rapamycin compositions of the invention contain a fatty acid ester at a concentration exceeding 10% or exceeding 12% by weight of the composition.

Rapamycin and its derivatives (including analogs) and prodrugs suitable for use in the compositions and methods of the invention include rapamycin (sirolimus) and prodrugs or derivatives thereof which are inhibitors of the mTOR cellular signaling pathway, and preferably inhibitors of mTOR itself. In one embodiment, a rapamycin derivative or prodrug is an mTOR inhibitor selected from the group consisting of everolimus (Affinitor; RAD001), temsirolimus (CCI-779), ridaforolimus (previously known as deforolimus; AP23573), umirolimus (Biolimus A9), zotarolimus (ABT-578), novolimus, myolimus, AP23841, KU-0063794, INK-128, EX2044, EX3855, EX7518, AZD08055 and OSI027. Further derivatives are known to the skilled person and include, for example, an O-substituted derivative in which the hydroxyl group on the cyclohexyl ring of sirolimus is replaced by —$OR_1$, in which $R_1$ is optionally a substituted alkyl, acylaminoalkyl, or aminoalkyl.

In one embodiment, the compound for use in the aerosol formulations and methods of the invention is a rapamycin derivative selected from the group consisting of everolimus, temsirolimus, ridaforolimus, umirolimus, and zotarolimus. The chemical structures of everolimus, temsirolimus, ridaforolimus, umirolimus, and zotarolimus are shown below.

-continued
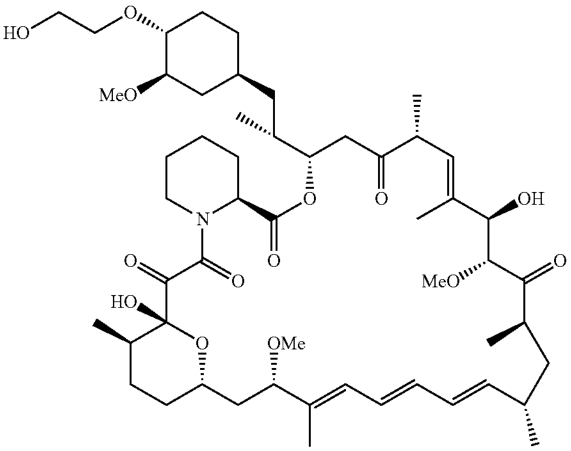
Everolimus (Affinitor)
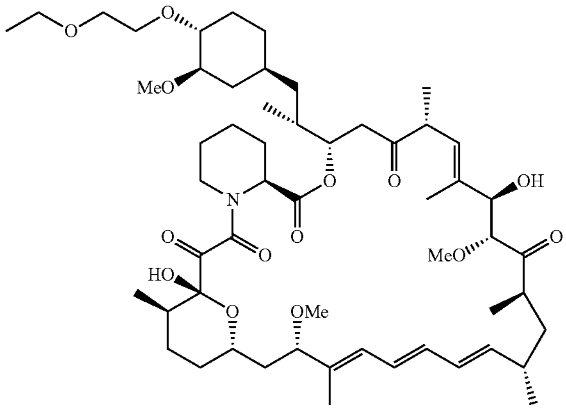
Umirolimus
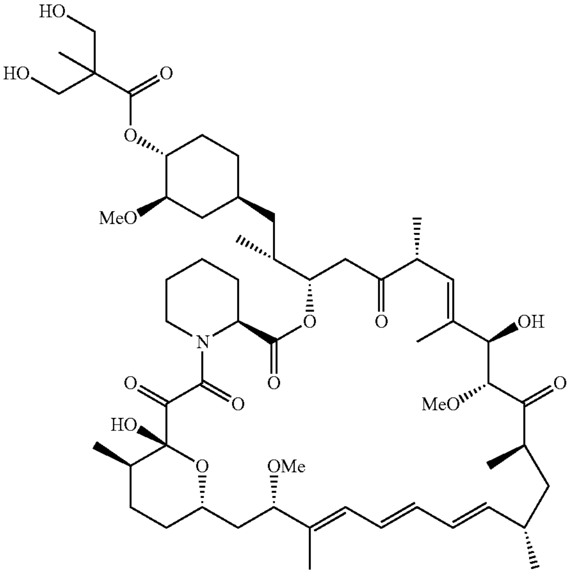
Temsirolimus (CCI-779)
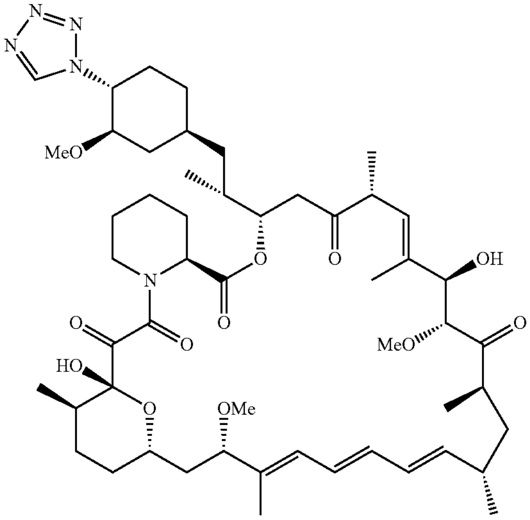
Zotarolimus (ABT-578)
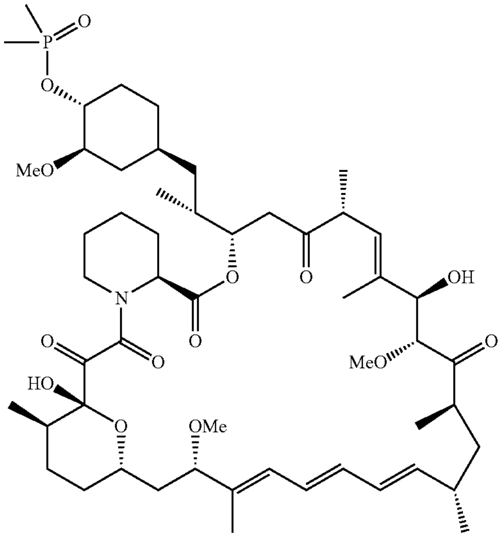
Ridaforolimus (MK-8669)
In one embodiment, the compound for use in the aerosol formulations and methods of the invention is an mTOR inhibitor selected from the group consisting of KU-0063794, AZD8055, INK128, and OSI-027. The chemical structures of the mTOR inhibitors KU-0063794, AZD8055, INK128, and OSI-027 are shown below.
KU-0063794
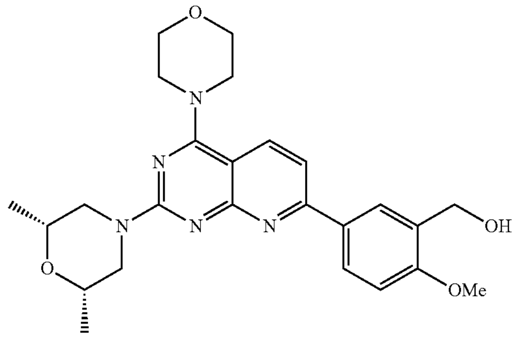

-continued

AZD8055

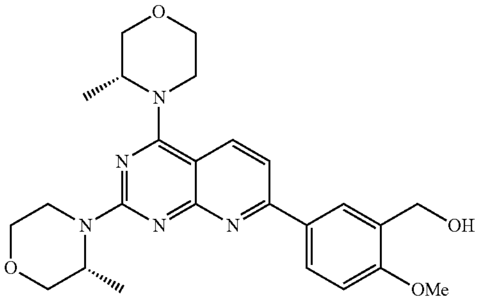

INK128

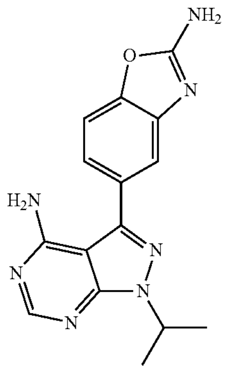

OSI-027

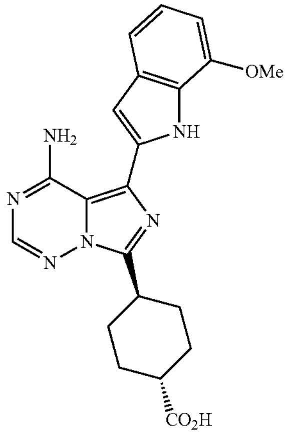

Particularly preferred for use in the methods and compositions of the invention are sirolimus, temsirolimus, and everolimus. In one embodiment, the compound for use in the aerosol formulations and methods of the invention is selected from the group consisting of sirolimus, temsirolimus, and everolimus. In one embodiment, the compound is sirolimus or everolimus.

Compositions for Inhalation

The invention provides pharmaceutical compositions adapted for administration by inhalation comprising rapamycin, or a prodrug or derivative thereof, in the form of an aqueous solution, a dry powder, or a mixture of one or more pharmaceutically acceptable propellants and a carrier. In one embodiment, the rapamycin is encapsulated in a pharmaceutically acceptable compound, material, or matrix. In one embodiment, the rapamycin is encapsulated in a liposomal formulation or a non-liposomal formulation.

The compositions of the invention are aerosolizable formulations of rapamycin suitable for pulmonary drug delivery in a human subject by inhalation. The term "aerosol" is used in this context to mean a colloidal system in which the dispersed phase is composed of either solid or liquid particles and in which the dispersal medium is a gas. In one embodiment, the gas is air and the formulation is a solution formulation suitable for administration via a nebulizer or a dry powder formulation suitable for administration via dry powder inhaler device. Generally, respirable particles or droplets will have a mean diameter in the range of 0.10 to 10 microns. The size of the particles or droplets is selected to maximize targeted delivery either to the lungs themselves (i.e., where the lung is the target tissue) or systemically (where the lungs are utilized as an alternative route for systemic administration). The size will preferably be in the range of about 0.5 to 5 microns where the lung itself is the therapeutic target, or less than 3 microns for systemic delivery via the lung. Size is measured according to methods known in the art and described, for example, in the U.S. Pharmacopeia at Chapters 905 and 601. For example, it is measured as Mass Median Aerodynamic Diameter (MMAD). In one embodiment, the average or mean diameter of the particles comprising the compositions described herein is measured as MMAD.

In one embodiment, the dispersed phase of the aerosol is composed of liquid particles or droplets. In this context, the terms "liquid particles" and "droplets" are used interchangeably. In this embodiment, the formulation of the invention is a solution formulation. In one embodiment, the dispersed phase of the aerosol is composed of solid particles. In this embodiment, the formulation of the invention is a dry powder formulation. Micronized particles of this size can be produced by methods known in the art, for example by mechanical grinding (milling), precipitation from subcritical or supercritical solutions, spray-drying, freeze-drying, or lyophilization.

Generally, inhaled particles are subject to deposition by one of two mechanisms: impaction, which usually predominates for larger particles, and sedimentation, which is prevalent for smaller particles. Impaction occurs when the momentum of an inhaled particle is large enough that the particle does not follow the air stream and encounters a physiological surface. In contrast, sedimentation occurs primarily in the deep lung when very small particles which have traveled with the inhaled air stream encounter physiological surfaces as a result of random diffusion within the air stream. The aerosol formulations of the invention are preferably adapted to maximize their deposition either by impaction (in the upper airways) or by sedimentation (in the alveoli), in order to achieve the desired therapeutic efficacy.

The amount of drug delivered to the patient from a delivery device, such as a nebulizer, pMDI or DPI device, is referred to as the delivered dose. It can be estimated in vitro by determining the amount of drug emitted from the delivery device in a simulated inhalation maneuver. This is termed emitted dose (ED) as measured according to methods known in the art, for examples those set out in the U.S. and European Pharmacopeias, e.g., at Chapter 601 and Chapter 905 of the USP. Accordingly, "emitted dose" is considered equivalent to the delivered dose.

The amount of drug delivered from the delivery device to the lungs of the patient is termed the respirable dose. It can be estimated in vitro by determining the fine particle dose (FPD) as measured using cascade impactors, such as a Next Generation Impactor (NGI) according to methods known in the art, for examples those set out in the U.S. and European Pharmacopeias, e.g., at Chapters 601 and 905 of the USP.

The amount of drug released in fine, inhalable particles from a delivery device is referred to as the fine particle fraction (FPF) of the formulation. FPF is the fraction of drug in the delivered dose that is potentially respirable. Thus, FPF is the ratio of FPD to ED (emitted, or delivered dose). These characteristics of the formulation are measured according to methods known in the art, for examples those set out in the U.S. and European Pharmacopeias, e.g., at Chapter 601 of the USP and monograph 2.9.18 of the Pharm Europa.

In one embodiment, the aerosolizable rapamycin formulations of the present invention have an FPF greater than 20% with a corresponding FPD ranging from 10 micrograms to 2 milligrams, preferably less than 0.5 milligrams, even after prolonged storage, e.g., after 1 to 12 months or after 1 to 36 months of storage. In one embodiment the dose delivered to the patient, the delivered dose (DD) or emitted dose (ED), ranges from 25 micrograms to 2.5 milligrams, preferably less than 0.5 milligrams.

In certain embodiments the rapamycin is encapsulated in a pharmaceutically acceptable compound, material, or matrix. In one embodiment, the rapamycin is encapsulated in a liposomal formulation or non-liposomal formulation.

Aqueous Solution Compositions

In one embodiment, the aerosolizable composition of the invention is an aqueous solution formulation of rapamycin adapted for pulmonary delivery via a nebulizer, including jet, vibrating mesh, and static mesh or orifice nebulizers. Thus, the solution formulation is adapted to enable aerosol droplet formation in the respirable range of from about 0.1 to 10 micron diameter, as described above. In one embodiment, the composition is a nebulizable aqueous solution formulation consisting of rapamycin (sirolimus) or a prodrug or derivative thereof, dissolved in water, ethanol, and a low molecular weight polyol, and optionally including a surface active agent. In one embodiment, the aqueous solution formulation has a viscosity below 20 mPa-s, below 10 mPa-s, or below 5 mPa-s, and a surface tension of at least 45 dynes/cm, preferably greater than 60 dynes/cm. Preferably, the formulation has a viscosity below 5 mPa-s, and a surface tension above 45 dynes/cm. In one embodiment, the composition has a viscosity below 20 mPa-s, a viscosity below 10 mPa-s, or a viscosity below 5 mPa-s and a surface tension of at least 45 dynes/cm, preferably greater than 60 dynes/cm.

In one embodiment, the aqueous solution formulation consists of rapamycin, water, ethanol, and a low molecular weight polyol selected from glycerol and propylene glycol. In one embodiment, the aqueous solution formulation consists of rapamycin, water, and a low molecular weight polyol selected from glycerol and propylene glycol, with the ethanol being optional. The formulation may also optionally contain a non-ionic surfactant, preferably PEG 100, or a polysorbate, preferably Polysorbate 80 ("PS80"), a phospholipid, preferably a natural phospholipid such as lecithin, and preferably hydrogenated soya lecithin, and an antioxidant or stabilizer, preferably disodium EDTA. In one embodiment, the non-ionic surfactant is selected from the group consisting of polyethylene glycol (PEG) PEG 100, PEG 1000, and Polysorbate 80 (also referred to as Tween™ 80, sorbitan monooleate, or polyoxyethylene sorbitan oleate), and mixtures thereof.

The amount of rapamycin in the aqueous solution is from about 0.001% to 0.01% weight percent (% wt or % w/w) based on the total weight of the solution. In one embodiment, rapamycin is present in solution at a concentration of about 0.01 mg/ml to about 0.1 mg/ml. In one embodiment, the amount of rapamycin is from 0.001% to 0.01% w/w based upon total weight of the solution.

In one embodiment, the concentration of rapamycin in solution is from about 0.01 to 0.1 mg/ml, the amount of the low molecular weight polyol is from 5 to 35% w/w, the amount of ethanol is present in the amount of 5-20% w/w, and the amount of the non-ionic surfactant is from 1 to 200 parts per million (ppm) w/w. Preferably, the amount of non-ionic surfactant is less than 100 ppm (w/w). The amounts of the optional antioxidant/stabilizer from zero to less than 0.01% w/w.

In one embodiment, the aqueous solution formulation of the invention does not contain one or more additives or excipients selected from the group consisting of polyethylene glycol, lecithin, EDTA, a block copolymer, and a cyclodextrin.

The aqueous solution formulation is a single phase aqueous solution in which the rapamycin is completely dissolved. The main co-solvents in the formulation are ethanol and a low molecular weight polyol selected from glycerol and propylene glycol. The rapamycin is not in suspension or emulsion, nor can the solution be described as a colloidal solution or dispersion. The aqueous solution formulation of the invention lacks colloidal structures such as micelles or liposomes. The amount of phospholipid, if present, is too small to form liposomes or to precipitate the rapamycin. And the combined amount of phospholipid and non-ionic surfactant is too small to modify surface tension. Consequently, neither the phospholipid nor the non-ionic surfactant is present in amounts sufficient to act as a surfactant in the traditional sense. In this context, the term surfactant refers to an agent that acts to lower the surface tension of the solution or the interfacial tension between the liquid and any solid drug particles in solution such that the surfactant acts as a detergent, wetting agent, emulsifier, or dispersing agent. Instead, the non-ionic surfactant in the solution formulation of the invention serves to block adsorption of the drug to the polyethylene container in which the final product is packaged, thereby preventing loss of drug potency via adsorption to the container.

Accordingly, in one embodiment the aqueous solution formulation is a single phase aqueous solution in which the rapamycin is completely dissolved, the solution lacks micelles or liposomes, and the solution is not an emulsion, dispersion, or suspension.

In one embodiment, the solution formulation is sterile. In one embodiment, the solution formulation is sterile filtered through a 0.2 micron filter. In one embodiment, the solution formulation is not sterilized by heat, such as by autoclaving, or by radiation.

In one embodiment, the invention provides a package containing one or more containers or vials (these terms are used interchangeably) filled with the sterile aqueous solution formulation. Preferably, the containers are unit dose containers. In one embodiment, the containers are polymer vials, preferably polyethylene vials. In one embodiment, the container or vial filled with the sterile aqueous solution formulation of the invention is produced by a process comprising the steps of forming the vial by blow molding and immediately thereafter filling the vial with the sterile-filtered formulation of the invention under aseptic conditions, followed by thermal sealing of the vial immediately after it is filled.

In one embodiment, the aqueous aerosol formulation of the invention comprises or consists of the following rapamycin (or a prodrug or derivative thereof) from about 0.001% to 0.01% w/w, propylene glycol from about 5% to 35% w/w, ethanol from about 5% to 20% w/w, Polysorbate 80 from about 1 to 200 ppm w/w, lecithin from about 1 to 100 ppm w/w, and water, where the amount of water is sufficient to achieve a concentration of the rapamycin between and 0.01 to 0.1 milligrams/milliliter. Optionally, a stability enhancer could be added such as disodium EDTA at levels below 0.01% wt/wt.

For aqueous and other non-pressurized liquid systems, a variety of nebulizers (including small volume nebulizers) are available to aerosolize the formulations. Compressor-driven nebulizers incorporate jet technology and use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers rely on mechanical energy in the form of vibration of a piezoelectric crystal to generate respirable liquid droplets and are commercially available from, for example, Omron Healthcare, Inc. and DeVilbiss Health Care, Inc.

In one embodiment, the aqueous aerosol formulation of the invention is delivered via a vibrating nebulizer available from Aerogen, Pari, Philips, or Omron. In one embodiment, the aqueous aerosol formulation of the invention is packaged in a container suitable for use with a vibrating mesh nebulizer, for example, the Aeroneb® Go (Aerogen, distributed by Philips Respironics), I-Neb® (Philips) or E-Flow® (Pari), or similar nebulizer. In one embodiment the aqueous aerosol formulation of the invention is delivered via an orifice nebulizer such as the Respimat® from Boeringher-Ingelheim.

Thus, in one embodiment the invention provides a pharmaceutical composition in the form of a nebulizable aqueous solution suitable for administration by inhalation to a human subject, the aqueous solution consisting of rapamycin or a prodrug or derivative thereof, preferably selected from sirolimus, everolimus, and temsirolimus, water, ethanol, and a low molecular weight polyol. In one embodiment, the low molecular weight polyol is glycerol or propylene glycol, or a mixture thereof. In one embodiment, the composition further comprises a nonionic surfactant selected from the group consisting of PEG 100, PEG 1000, and polysorbate 80, and mixtures thereof. In one embodiment, the amount of nonionic surfactant in the formulation is from 1 to 200 ppm w/w, preferably less than 100 ppm w/w, based upon the weight of the formulation. In one embodiment, the composition further comprises a phospholipid, an antioxidant or chemical stabilizer. In one embodiment, the amount of antioxidant or chemical stabilizer in the formulation is less than 0.01% w/w based upon the weight of the formulation. In one embodiment, the antioxidant or chemical stabilizer is EDTA. In one embodiment, the amount of rapamycin in the formulation is from 0.001 to 0.01% w/w based upon the weight of the formulation.

In one embodiment, the composition does not contain one or more additives or excipients selected from the group consisting of polyethylene glycol, lecithin, EDTA, a block copolymer, and a cyclodextrin.

In one embodiment, the composition lacks colloidal structures selected from micelles and liposomes.

In one embodiment, the composition is suitable for administration via any one of a jet nebulizer, a vibrating mesh nebulizer, a static mesh nebulizer, and an orifice nebulizer.

In one embodiment, the composition has a viscosity below 20 mPa-s, preferably below 10 mPa-s, most preferably below 5 mPa-s, and a surface tension of at least 45 dynes/cm, preferably at least 50 dynes/cm.

The invention also provides a method of manufacturing a pharmaceutical composition of the invention in the form of a nebulizable aqueous solution, the method comprising sterile filtering the solution through a filter with pore size of 0.2 microns or less and collecting the sterile filtrate in collection vessel under aseptic conditions. In one embodiment, the method of manufacturing further comprises transferring the sterile filtrate into a container closure under aseptic conditions. In one embodiment, the container closure is a unit-dose polyethylene vial. In one embodiment, the vial is produced by blowmolding immediately before the sterile filtrate is transferred to the vial. In one embodiment, the method further comprises the step of thermally sealing the vial immediately after the sterile filtrate is transferred to the vial.

Dry Powder Compositions

In one embodiment, the aerosolizable composition of the invention is a dry powder comprising micronized particles of rapamycin, or a prodrug or derivative thereof, as the therapeutic agent (also referred to as "drug"), the particles having diameters from 0.1 to 10 microns and a mean diameter of between about 0.5 to 4.5 microns, about 1 to 4 microns, about 1 to 3.5 microns, about 1.5 to 3.5 microns, or about 2 to 3 microns. The dry powder formulation is suitable for use in either a dry powder inhaler device (DPI) or a pressurized metered dose inhaler (pMDI). The amount of rapamycin in the dry powder is from about 0.5 to 20% (w/w) based on total weight of the powder. In one embodiment, the amount of rapamycin is about 1% or 2% (w/w).

In one embodiment, micronized rapamycin is produced by wet polishing or jet milling as described below to generate diameters in the range of about 0.5 to 4.5 microns, about 1 to 4 microns, or about 2 to 3 microns, and the rapamycin particles are blended onto lactose carrier particles in a drug/carrier ratio ranging from 0.5-2% w/w with a preferred ratio of 1%.

In one embodiment, the drug particles are lightly compacted into a frangible matrix which is contained within the delivery device (a dry powder inhaler). Upon actuation the delivery device abrades a portion of the drug particles from the matrix, and disperses them in the inspiratory breath delivering the drug particles to the respiratory tract. Alternatively the drug particles may be a free flowing powder contained within a reservoir in the delivery device (a dry powder inhaler). The reservoir can be an integral chamber within the device, or a capsule, blister or similar preformed reservoir that is inserted into the device prior to actuation. Upon actuation the device dispersed a portion of the drug particles from the reservoir and disperses them in the inhalation breath delivering the drug particles to the respiratory tract.

In one embodiment, the dry powder composition consists of drug particles and a carrier selected from the group consisting of arabinose, glucose, fructose, ribose, mannose, sucrose, trehalose, lactose, maltose, starches, dextran, mannitol, leucine, lysine, isoleucine, dipalmitylphosphatidylcholine, lecithin, polylactic acid, poly (lactic-co-glutamic) acid, and xylitol, or mixtures of any of the foregoing. In one embodiment, the carrier is lactose, particularly in the form of the monohydrate. In one embodiment, the dry powder composition comprises a blend of two or more carriers.

In one embodiment the dry powder composition comprises drug and a blend of at least two different carriers. In one embodiment, the drug to carrier ratio is in the range of from about 0.5 to 20% (w/w). In one embodiment, the drug particles have diameters ranging from 0.1 to 10 microns with a mean diameter of about 1 to 4, 1 to 3.5, or 1.5 to 3.5, or 2 to 3 microns. The carrier particles may have diameters ranging from 2 to 200 microns.

In one embodiment, the composition is contained in a blister pack or a reservoir of a DPI device. In one embodiment, the dry powder composition is preloaded into a gelatin, starch, cellulosic, or polymeric capsule, or a foil/foil or foil/plastic blister suitable for use in a DPI device. Each capsule or blister may contain from 1 to 100 milligrams of the dry powder composition. The capsules or blisters may be inserted into a dry powder inhaler (DPI) device such as Aerolizer®, Plastiape® RS01 Model 7, and Plastiape® RS00 Model 8, XCaps®, FlowCaps®, Arcus®, Diskhaler® or Microdose®. Upon actuating the DPI device, the capsules or blisters are ruptured and the powder is dispersed in the inspiratory breath, delivering the drug to the respiratory tract.

In one embodiment, the dry powder composition is contained in a dry powder inhaler (DPI) device selected from Accuhaler®, Conix™, Rotahaler®, TwinCaps®, XCaps®, FlowCaps®, Turbuhaler®, NextHaler®, CycloHaler®, Revolizer™, Diskhaler®, Diskus®, Spinhaler, Handihaler®, Microdose Inhaler, GyroHaler®, OmniHaler®, Clickhaler®, Duohaler® (Vectura), and ARCUS® inhaler (Civitas Therapeutics). In one embodiment, the invention provides a DPI device containing a dry powder composition described herein. In one embodiment the device is selected from the group consisting of XCaps, FlowCaps, Handihaler, TwinCaps, Aerolizer®, Plastiape® RS01 Model 7, and Plastiape® RS00 Model 8. In one embodiment, the device containing the composition is selected from the group consisting of a GyroHaler®, an OmniHaler®, a Clickhaler®, a Duohaler®, and an ARCUS® inhaler.

The carrier particles are preferably of larger size (greater than 5 microns) so as to avoid deposition of the carrier material in the deep lung. In one embodiment, the carrier particles have diameters ranging from 1 to 200 microns, from 30 to 100 microns, or less than 10 microns. In one embodiment the carrier particles are a blend of two carriers, one with particles of about 30-100 microns and the other with particles less than 10 microns. The ratio of the two different carriers is in the range of from 3:97 to 97:3. In one embodiment, the dry powder composition consists of 0.5-20% (w/w) drug to carrier ratio, the drug particles having diameters from 0.1 to 10 microns with a mean diameter less than 3.5 microns. In one embodiment, the carrier material is a crystalline carrier material. Preferably, the crystalline carrier material is one which is at least 90%, preferably greater than 95% crystalline and in which no or substantially no water is absorbed by the carrier under conditions of 80% or lower relative humidity at room temperature. Examples of such crystalline carriers are lactose monohydrate and glucose monohydrate. The amount of carrier is from 1 to 99.0% or more of the formulation by dry weight of the powder, preferably 5 to 99%, 10 to 99%, 20 to 99%, 30 to 99%, 40 to 99%, or 50 to 99%.

In one embodiment, the dry powder composition is contained within a reservoir in the delivery device (a dry powder inhaler). The reservoir can be an integral chamber within the device, or a capsule, blister or similar preformed reservoir that is inserted into the device prior to actuation. Upon actuation the device dispersed a portion of the drug particles from the reservoir and disperses them in the inspiratory breath delivering the drug particles to the respiratory tract.

In one embodiment, drug is present as a fine powder with a pharmaceutically acceptable carrier. In the context, the term "fine" refers to a particle size in the inhalable range, as discussed above. Preferably, the drug is micronized such that the particles have a mean diameter in the range of 10 microns or less. In one embodiment, the mean diameter (MMAD or Dv50) of the particles of rapamycin (or a prodrug or derivative thereof) in dry powder composition described herein is from 0.5 to 10 microns, from 0.5 to 6 microns, from 1 to 5 microns, from 1 to 4 microns, from 1 to 3 microns, or from 2 to 3 microns. The MMAD or Dv50 value is the particle size below which 50% of the volume of the population occurs.

In one embodiment, the dry powder formulation of rapamycin further comprises one or more additives selected from the additives described below. In one embodiment, the one or more additives comprises or consists of magnesium stearate. In one aspect of this embodiment, the magnesium stearate is present in amounts of 0.001 to 10% by dry weight of the powder, preferably in amounts of from 0.01 to 5% or 0.01 to 2%. In another embodiment, the additive comprises or consists of a phospholipid, such as lecithin (which is a mixture of phosphatidylcholines) in an amount of 0.1% to 1% by dry weight of the powder, preferably 0.2% to 0.6%. In one aspect of this embodiment, the additive is coated onto the carrier material prior to or simultaneously with a step of blending the carrier with the particles of rapamycin. This can be accomplished, for example, by utilizing a high energy mixing step to coat the carrier with the additive, or a long duration of low energy mixing, or a combination of low and high energy mixing to achieve the desired level of coated carrier material. Low energy devices for mixing dry powders to form blends are known in the art and include, for example, V-blenders, double cone blenders, slant cone blenders, cube blenders, bin blenders, horizontal or vertical drum blenders, static continuous blenders, and dynamic continuous blenders. Other, higher energy devices include high shear mixers known to those skilled in the art.

In certain embodiments, the dry powder is contained in a capsule. In one embodiment the capsule is a gelatin capsule, a plastic capsule, or a cellulosic capsule, or is in the form of a foil/foil or foil/plastic blisters. In each instance, the capsule or blister is suitable for use in a DPI device, preferably in dosage units together with the carrier in amounts to bring the total weight of powder in each capsule to from 1 mg to 100 mg. Alternatively, the dry powder may be contained in a reservoir of a multi-dose DPI device.

The particle size of the rapamycin can be reduced to the desired microparticulate level by conventional methods, for example by grinding in an air-jet mill, ball mill or vibrator mill, by wet polishing, microprecipitation, spray drying, lyophilization or recrystallization from subcritical or supercritical solutions. Jet milling or grinding in this context refers to micronization of dry drug particles by mechanical means. Micronization techniques do not require making a solution, slurry, or suspension of the drug. Instead, the drug particles are mechanically reduced in size. Due to the relatively high energy that is employed by micronization, in certain embodiments it is desirable to include a carrier material in a co-micronized mixture with the rapamycin. In this context, the carrier material absorbs some of the energy of micronization which otherwise could adversely affect the structure of the rapamycin. In one embodiment, rapamycin particles in a size range of from 1 to 4 or from 2 to 3 microns are produced by a jet milling method.

Wet polishing as described in US2013/0203717 involves using high shear to reduce the particle size of the drug particles in a suspension or slurry. Wet polishing can include just the drug particles or additional particulates termed milling media. In one embodiment, the particle size of the rapamycin can be reduced to the desired level using a wet polishing process, which comprises wet milling, specifically by cavitation at elevated pressure, where rapamycin is suspended in water or other solvent where it is insoluble, and then is followed by spray drying of the suspension to obtain rapamycin as a dry powder. In one embodiment, rapamycin particles in a size range of from 1 to 4 or from 2 to 3 microns are produced by a wet polishing method that comprises preparing a suspension of rapamycin, subjecting the suspension to microfluidization, and spray-drying the resulting particles to form a dry powder. The rapamycin may be suspended in an anti-solvent selected from the group consisting of propyl or butyl alcohol, water, and ethyl acetate. In one embodiment, the suspension is an aqueous suspension.

Spray drying generally involves making a solution, slurry, or suspension of the drug, atomizing the solution, slurry, or suspension, to form particles and then evaporating the solution, slurry, or suspension media to form the particles. The solution, slurry or suspension, can be formed under subcritical or supercritical conditions. The evaporation step can be accomplished by elevating the temperature of the atmosphere into which the atomization occurs, or by decreasing the pressure, or a combination of both. In one embodiment, the powder formulation comprising rapamycin is made by spray drying an aqueous dispersion of rapamycin to form a dry powder consisting of aggregated particles of rapamycin having a size suitable for pulmonary delivery, as described above. The aggregate particle size can be adjusted (increased or decreased) to target either the deep lung or upper respiratory sites, such as the upper bronchial region or nasal mucosa. This can be accomplished, for example, by increasing the concentration of rapamycin in the spray-dried dispersion or by increasing the droplet size generated by the spray dryer.

Alternatively, the dry powder can be made by freeze-drying (lyophilization) the aqueous drug solution, dispersion, or emulsion, or by a combination of spray-drying and freeze-drying.

In one embodiment, the dry powder formulation is made by freeze-drying an aqueous dispersion of rapamycin, and one or more optional additives. In one embodiment, the powders contain aggregates of rapamycin and an additive, if present, wherein the aggregates are within a respirable size range as described above.

In one embodiment, the aqueous dispersion of rapamycin and the one or more optional additives further comprises a dissolved diluent such as lactose or mannitol such that when the dispersion is freeze-dried, respirable diluent particles, each containing at least one embedded drug particle and additive particle, if present, are formed.

In one embodiment, the dry powder comprises rapamycin loaded liposomes. Drug-loaded liposomes can be produced by methods known in the art, for example using the technique described for tacrolimus in M. Chougale, et al. *Int. J. Nanomedicine* 2:625-688 (2007). Briefly, rapamycin, hydrogenated phosphatidylcholine (HSPC), and cholesterol are dissolved in a mixture of methanol and chloroform and then subjected to dry thin film formation, e.g., in Rotaevaporator. The liposomes are hydrated and the liposomal dispersion is passed through a high-pressure homogenizer for size reduction. The resultant pellets are characterized for vesicle size and percent drug entrapment and pellets equivalent to the desired amount of rapamycin are then dispersed in a suitable medium and subjected to spray-drying to obtain particles of the desired size for inhalation. The spray dried powder can be filled into capsules, canisters, or blister packs for administration.

In one embodiment the dry powder particles can be produced by precipitation from a supercritical or subcritical solution.

The dry powder compositions may be contained in a suitable dry powder inhaler device, or in a capsule or blister for use in such a device. Examples of such devices are provided above and include Accuhaler®, Aerolizer®, the Plastiape® RS01 Model 7, the Plastiape® RS00 Model 8, Conix™, Rotahaler®, TwinCaps®, XCaps®, FlowCaps®, Turbuhaler®, NextHaler®, CycloHaler®, Revolizer™, Diskhaler®, Diskus®, Spinhaler, Handihaler®, Microdose Inhaler, GyroHaler®, OmniHaler®, Clickhaler®, or Duohaler® (Vectura), or a breath-actuated ARCUS® inhaler (Civitas Therapeutics). In one embodiment, the invention provides a DPI device containing a dry powder composition described herein. In one embodiment the device is selected from the group consisting of XCaps, FlowCaps, Handihaler, TwinCaps, Aerolizer®, the Plastiape® RS01 Model 7, and the Plastiape® RS00 Model 8.

Propellant-Based Formulations

In another embodiment of the invention, the rapamycin is formulated in a propellant-based formulation which may also be referred to generically herein as "a pMDI formulation". A pMDI formulation is suitable for delivery by a device such as a pressurized metered dose inhaler (pMDI). In one embodiment, the composition comprises rapamycin, a propellant, and a vegetable oil or pharmaceutically acceptable derivative of a vegetable oil. The propellant is preferably selected from 1,1,1,2-tetrafluoroethane (HFA134a) and 1,1,1,2,3,3,3-heptafluoropropane (HFA227), or mixtures thereof. In one embodiment, the vegetable oil is selected from olive oil, safflower oil, and soybean oil. The rapamycin may be in solution or in suspension in the propellant. In this context, "in suspension" refers to where the rapamycin is present in particulate form dispersed in the propellant. In one embodiment, the rapamycin is micronized and is present in suspension in the propellent. In one embodiment, the formulation further comprises a wetting agent or co-solvent such as ethanol. In one embodiment, the formulation further comprises a polyhydroxy alcohol such as propylene glycol.

Suitable propellants are known in the art and include, for example, halogen-substituted hydrocarbons, for example fluorine-substituted methanes, ethanes, propanes, butanes, cyclopropanes or cyclobutanes, particularly 1,1,1,2-tetrafluoroethane (HFA134a) and 1,1,1,2,3,3,3-heptafluoropropane (HFA227), or mixtures thereof.

In one embodiment, the formulation comprises micronized rapamycin, ethanol, a suitable propellant such as HFA 134a, HFA 227, or a mixture of suitable propellants, and optionally one or more surfactants. In one embodiment, the formulation further comprises a lubricant.

In one embodiment, the formulation comprises rapamycin, a propellant, and a vegetable oil. In one aspect, the formulation does not comprise an additive or surfactant. For example, the formulation does not comprise ethanol, a polyhydroxy alcohol (e.g., propylene glycol), or a surfactant (e.g., sorbitan trioleate, sorbitan monooleate, or oleic acid).

In one embodiment, the propellant-based formulation comprises compressed air, carbon dioxide, nitrogen or a liquefied propellant selected from the group consisting of n-propane, n-butane, isobutane or mixtures thereof, or 1,1,1,2-tetrafluoroethane (HFA134a) and 1,1,1,2,3,3,3-heptafluoropropane (HFA227), or mixtures thereof, with or without a polar co-solvent such as an alcohol. The composition can be a solution or a suspension. For suspensions the drug particles have diameters from 0.1 to 10 microns with a mean diameter less than 3.5 microns.

The propellant-based formulation is prepared by methods known in the art, for example by wet milling the coarse rapamycin, and optional additive, in liquid propellant, either at ambient pressure or under high pressure conditions. In certain embodiments, the additive is a surfactant which serves to prevent aggregation (caking or crystallization), to facilitate uniform dosing, and (or alternatively) to provide a favorable fine particle fraction (FPF). In one aspect, the surfactant is selected from sorbitan trioleate, sorbitan monooleate, or oleic acid. Alternatively, dry powders containing drug particles are prepared by spray-drying or freeze-drying aqueous dispersions of the drug particles as discussed above and the resultant powders dispersed into suitable propellants for use in conventional pressurized metered dose inhalers (pMDIs). In one embodiment, the inhalation device is a Respimat™.

In one embodiment, the propellant-based aerosol rapamycin formulations of the invention are stable against particle size growth or change in the crystal morphology of the rapamycin over prolonged periods of time.

Process for Manufacturing Sterile Unit Dose Forms

In one embodiment, the compositions of the invention are sterile compositions. In one embodiment, the sterile compositions are sterile unit dose forms. In one embodiment, the sterile unit dosage form is a capsule suitable for use in a nebulizer device.

In one embodiment, the finished composition is sterilized in its container-closure by heat, e.g., autoclaving, or by radiation. In one embodiment, the component parts of the composition are first sterilized by a suitable process including sterile filtration for liquid components and radiation or autoclaving for solids or liquids, the process further comprising maintaining the sterility of the sterile components by packaging in hermetic containers, combining the components in a mixing vessel in the appropriate proportions, and filling the resulting product into a container closure, all performed in an aseptic suite. This process has the disadvantage of being expensive and requiring difficult aseptic handling techniques. Accordingly, it is used primarily to process particulate suspensions or colloidal dispersions, liposomal formulations, or emulsions, which cannot be passed through a submicron filter for sterilization. Finally, in one embodiment, the finished composition is sterile filtered through a submicron filter, preferably a 0.2 micron filter. In one embodiment, the compositions of the invention are single-phase aqueous solutions sterilized via a filtration sterilization process. In contrast, emulsions and liposomal formulations are typically not sufficiently stable under the high shear conditions of a filtration sterilization process and so are not preferred for this process.

In one embodiment, the compositions of the invention are single-phase aqueous solutions which are filled into a container-closure, e.g., a vial, formed of a polymer, preferably polyethylene, or alternatively a glass vial. Autoclaving and radiation are not suitable where the vial is a polymer vial because of the high likelihood of creating chemical instability in the drug and/or formulation excipients, as well as in the container, and due to the generation of undesirable impurities. In one embodiment, the compositions of the invention are sterilized by a process that does not include heat (autoclaving) or radiation, and instead includes a filtration sterilization process. Preferably, in accordance with this embodiment, the single-phase aqueous solutions of rapamycin are sterilized by filtration through a filter having a pore size less than or equal to 0.2 microns. In one embodiment, the sterile filtrate is collected in a collection vessel located in an aseptic suite. In one embodiment, the sterile filtrate is transferred from the collection vessel into a container closure in an aseptic suite. Preferably the container closure is a polymer vial, preferably a unit dose vial, and most preferably a polyethylene unit dose vial. In one embodiment, the polymer vial is formed by blowmolding immediately before it is filled and then thermally sealed immediately after filling. This technique may be also referred to as "form-fill-seal" or a "blow-fill". This technique is particularly advantageous in the context of the compositions of the invention which are single-phase aqueous solutions of rapamycin because this process does not require heat or radiation, both of which may degrade either the drug itself, the formulation excipients, or the container closure.

Pulmonary Administration and Dosing

The present invention provides compositions and methods for the treatment and prophylaxis of LAM by administering rapamycin to the respiratory tract, preferably to the lungs, by inhalation. Pulmonary delivery is preferably accomplished by inhalation of the aerosol through the mouth and throat into the lungs, but may also be accomplished by inhalation of the aerosol through the nose. Thus, in one embodiment the aerosol is delivered intranasally. In another embodiment, the aerosol is delivered perorally.

The compositions and methods of the invention advantageously provide for the targeted delivery of a therapeutically effective amount of rapamycin to the lungs while simultaneously reducing to very low or undetectable levels the amount of rapamycin in the blood and available systemically. In one embodiment, the amount of rapamycin in a single dose of a dry powder composition described herein is from about 5 to 500 micrograms or from about 100 to 300 micrograms, or from about 50 to 250 micrograms. The targeted delivery of low dose rapamycin directly to the lungs while minimizing systemic exposure provides for an improved therapeutic index compared to oral dosage forms.

In one embodiment, administration of rapamycin by inhalation according to the methods of the invention increases the therapeutic index of rapamycin. In this context, as applied to human subjects, the therapeutic index is a ratio that compares the dose that produces a therapeutic effect ($ED_{50}$) to the dose that produces a toxicity ($TD_{50}$) in 50% of the population. The ratio is represented as $TD_{50}/ED_{50}$. In one embodiment, administration of rapamycin by inhalation according to the methods of the invention reduces one or more toxicities associated with orally administered rapamycin, thereby increasing the therapeutic index of rapamycin.

The invention includes aerosolizable formulations in the form of solutions and powders. Accordingly, the rapamycin may be administered according to the methods of the invention in the form of an aqueous aerosol, a dry powder aerosol, or a propellant-based aerosol.

In one embodiment, the administered dose of rapamycin produces a blood trough level in the subject of from of from 0.01 to 0.15 ng/ml, from 0.075 to 0.350 ng/ml, from 0.150 to 0.750 ng/ml, from 0.750 to 1.5 ng/ml or from 1.5 to 5 ng/ml. In one embodiment, the administered dose of rapamycin produces a blood trough level in the subject of less than 5 ng/ml, less than 2 ng/ml, less than 1 ng/ml, or less than 0.5 ng/ml.

In one embodiment, the administered dose of rapamycin is sufficient to produce a concentration of rapamycin in lung tissue in the range of from 1 ng/g to 1 ug/g, preferably from about 5 ng/g to 100 ng/g, from about 5 ng/g to about 20 ng/g, or from about 5 ng/g to about 30 ng/g.

In one embodiment, the administered dose of rapamycin is from 5 to 100 micrograms, from 20 to 100 micrograms, from 20 to 250 micrograms, from 50 to 500 micrograms (0.05 to 0.5 milligrams), from 250 to 1000 micrograms (0.25 to 1 milligrams) or from 500 to 2000 micrograms (0.5 to 2 milligrams). In one embodiment, the amount of rapamycin administered is less than 500 micrograms, less than 100 micrograms, less than 50 micrograms, less than 20 micrograms, or less than 10 micrograms. Preferably, the amount of rapamycin administered is less than 0.5 milligrams or less than 0.25 milligrams.

In one embodiment, the rapamycin is administered once daily.

In one embodiment, the total daily dose of rapamycin is in the range of from 5 to 100 micrograms, from 20 to 250 micrograms, from 50 to 500 micrograms (0.05 to 0.5 milligrams), from 250 to 1000 micrograms (0.5 to 1 milligrams) or from 500 to 2000 micrograms (0.5 to 2 milligrams). In one embodiment, the total daily dose of rapamycin is less than 500 micrograms, less than 100 micrograms, less than 50 micrograms, less than 20 micrograms, or less than 10 micrograms. In one embodiment, the total daily dose of rapamycin administered to the subject is less than 0.5 milligrams or less than 0.25 milligrams per day.

In one embodiment, a composition of the invention is administered once per day to the subject. In one embodiment, a composition of the invention is administered twice or three times a day. Preferably, the composition is administered once or twice daily, or less than once daily.

In one embodiment, the methods of the invention comprise administering rapamycin via a pulmonary route in combination with one or more additional therapeutic agents selected from the group consisting of a statin, progesterone, tamoxifen, gonadotropin-releasing hormone (GnRH) agonists, doxycycline, a src inhibitor, an autophagy inhibitor (e.g. hydroxychloroquine), a VEGF-C or -D inhibitor, and a VEGF receptor inhibitor. In one embodiment, the one or more additional therapeutic agents is selected from a statin, progesterone, tamoxifen, and gonadotropin-releasing hormone (GnRH) agonists. In one embodiment, the one or more additional therapeutic agents is selected from an estrogen antagonist, a statin, a src inhibitor, and a VEGF-R inhibitor. In one embodiment, the one or more additional therapeutic agents is selected from the group consisting of letrozole, tamoxifen, simvastatin, saracatinib, pazopanib, imatinib, and combinations thereof. The one or more additional agents may be administered by the same or a different route of administration as the rapamycin. For example, the agent may be administered by inhalation, intranasally, orally or intravenously.

In one embodiment, the methods of the invention comprise administering rapamycin via a pulmonary route in combination with one or more additional therapies. In one embodiment, the one or more additional therapies is selected from anti-estrogen therapy, hormonal therapy, anti-cancer chemotherapy, and radiation therapy. In one embodiment, the methods of the invention comprise administering rapamycin via a pulmonary route in combination with anti-estrogen therapy or hormone therapy.

In certain embodiments, the methods include pulmonary administration of a composition of the invention as the primary therapy. In other embodiments, the administration of a composition of the invention is an adjuvant therapy. In either case, the methods of the invention contemplate the administration of a composition of the invention in combination with one or more additional therapies for the treatment of a disease or disorder. The terms "therapy" and "therapies" refer to any method, protocol and/or agent that can be used in the prevention, treatment, management or amelioration of a disease or disorder, or one or more symptoms thereof. In certain embodiments, a therapy is selected from chemotherapy, radiation therapy, hormonal therapy, and anti-estrogen therapy.

Preferably, the administration of a pharmaceutical composition comprising rapamycin or a prodrug or derivative thereof according to the methods of the invention in combination with one or more additional therapies provides a synergistic response in the subject having LAM. In this context, the term "synergistic" refers to the efficacy of the combination being more effective than the additive effects of either single therapy alone. In one embodiment, the synergistic effect of combination rapamycin therapy according to the invention permits the use of lower dosages and/or less frequent administration of at least one therapy in the combination compared to its dose and/or frequency outside of the combination. In another embodiment, the synergistic effect is manifested in the avoidance or reduction of adverse or unwanted side effects associated with the use of either therapy in the combination alone.

Nebulizer Delivery

In one embodiment, the rapamycin is formulated as an aqueous solution suitable for nebulization and delivered via a nebulizer. For aqueous and other non-pressurized liquid systems, a variety of nebulizers (including small volume nebulizers) are available to aerosolize the formulations. Compressor-driven nebulizers incorporate jet technology and use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers rely on mechanical energy in the form of vibration of a piezoelectric crystal to generate respirable liquid droplets and are commercially available from, for example, Omron Healthcare, Inc. and DeVilbiss Health Care, Inc. The nebulizer may be, for example, a conventional pneumatic nebulizer such as an airjet nebulizer, or an ultrasonic nebulizer, which may contain, for example, from 1 to 50 ml, commonly 1 to 10 ml, of the solution formulation.

In one embodiment, the aqueous solution formulation of the invention is adapted for administration with a nebulizer comprising a vibrating or fixed mesh. For example, devices such as an AERx® (Aradigm), RESPIMAT® (Boehringer Ingelheim), I-Neb® (Philips), or MicroAire® (Omron) in which drug solution is pushed with a piston or pneumatic pressure, or with a piezoelectric crystal through an orifice or mesh. Alternatively, the solution can be pumped through a vibrating mesh nebulizer such as the E-Flow® (Pari) or Aeroneb® Go (Aerogen). These devices allow much smaller nebulized volumes, e.g., 10 to 100 ul, and higher delivery efficiencies than conventional nebulizers.

Dry Powder Delivery

In one embodiment, the dry powder compositions of the invention are delivered by a non-propellant based dry powder inhaler (DPI) device. In one embodiment, the powder is contained in capsules of gelatin or plastic, or in blisters, suitable for use in a DPI device. In one embodiment, the powder is supplied in unit dosage form and in dosage units of from 5 mg to 100 mg of powder per capsule. In another embodiment, the dry powder is contained in a reservoir of a multi-dose dry powder inhalation device. In one embodiment, the inhaler device comprises an aerosol vial provided with a valve adapted to deliver a metered dose, such as 10 to 100 μl, e.g. 25 to 50 μl, of the composition, i.e. a device known as a metered dose inhaler.

In one embodiment, the DPI device is a blister based device such as the GyroHaler® or the OmniHaler® (both from Vectura), a reservoir based device such as the Clickhaler® or Duohaler® (Vectura), and the ARCUS® inhaler (Civitas Therapeutics). In one embodiment, the DPI device is selected from Pulmatrix™, and Hovione Twincaps and XCaps™. In one embodiment the device is selected from the group consisting of XCaps, Plastiape® RS01 Model 7, and Plastiape® RS00 Model 8.

In one embodiment, the DPI device is selected from the group consisting of Accuhaler®, Aerolizer®, the Plastiape® RS01 Model 7, the Plastiape® RS00 Model 8, Conix™, Rotahaler®, TwinCaps®, XCaps®, FlowCaps®, Turbuhaler®, NextHaler®, CycloHaler®, Revolizer™, Diskhaler®, Diskus®, Spinhaler, Handihaler®, Microdose Inhaler, GyroHaler®, OmniHaler®, Clickhaler®, or Duohaler® (Vectura), or a breath-actuated ARCUS® inhaler (Civitas Therapeutics).

In one embodiment, the DPI device is selected from the group consisting of Arcus™, Aspirair™, Axahaler™, Breezhaler™, Clickhaler™, Conix Dry™, Cricket™, Dreamboat™, Genuair™, Gemini™, Inspiromatic™, iSPERSE™, MicroDose™, Next DPI™, Prohaler™, Pulmojet™, Pulvinal™, Solis™, Taifun™, Taper Dry™, Trivai™, Novolizer™, Podhaler™, Skyehaler™, Spiromax™, Twincaps/Flowcaps™, and Turbuhaler™. In one embodiment, the DPI device is adapted to deliver the dry powder from a capsule or blister containing a dosage unit of the dry powder or a multi-dose dry powder inhalation device adapted to deliver, for example, 5-25 mg of dry powder per actuation.

pMDI Delivery

In another embodiment, the rapamycin is delivered in the form of aerosolized particles from a pressurized container or dispenser that contains a suitable propellant as described above in connection with propellant-based formulations. In one embodiment, the inhaler is a propellant driven inhaler, such as a pMDI device, which releases a metered dose of rapamycin upon each actuation. A typical pMDI device comprises a canister containing drug, a drug metering valve, and a mouthpiece. In one aspect of this embodiment, the rapamycin is formulated as a suspension in the propellant. In the context of this embodiment, the rapamycin is made into a fine powder which is suspended in the liquefied propellant or propellant blend. The suspension is then stored in a sealed canister under sufficient pressure to maintain the propellant in liquid form. In another embodiment, the rapamycin is formulated as a solution. In the context of this embodiment, the rapamycin is solubilized in the liquefied propellant or propellant blend. In one embodiment, the formulation further comprises a stabilizer in an amount suitable to stabilize the formulation against settling, creaming or flocculation for a time sufficient to allow reproducible dosing of the rapamycin after agitation of the formulation. The stabilizer may be present in excess in an amount of about 10 part by weight to about 5000 parts by weight based on one million parts by total weight of the aerosol formulation. In one embodiment, the fluid carrier is 1,1,1,2-tetrafluoroethane, 1,1,1,2,3,3,3-heptafluoropropane or a mixture thereof. In another embodiment, the fluid carrier is a hydrocarbon (e.g., n-butane, propane, isopentane, or a mixture thereof). The composition may further comprise a co-solvent (e.g., ethanol or other suitable co-solvent).

In one embodiment of the methods of the invention, the aerosol formulation comprising rapamycin further comprises an additional drug. In one aspect of this embodiment, the additional drug is selected from the group consisting of corticosteroids, estrogen receptor antagonists, anticholinergics, beta-agonists, non-steroidal anti-inflammatory drugs, macrolide antibiotics, bronchodilators, leukotriene receptor inhibitors, muscarinic antagonists, cromolyn sulfate, and combinations thereof.

Additives

The aerosol compositions of the invention may contain one or more additives in addition to any carrier or diluent (such as lactose or mannitol) that is present in the formulation. In one embodiment, the one or more additives comprises or consists of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the aerosol compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides. Each of these is described in more detail below.

PEG Fatty Acid Esters

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Most preferred hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and diesters.

Polyethylene Glycol Glycerol Fatty Acid Esters

Preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil®b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids

Polyglycerol esters of fatty acids are also suitable surfactants for use in embodiments of the present invention. Among the polyglyceryl fatty acid esters, preferred hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Preferred hydrophilic surfactants include polyglyceryl-10 laurate (Nikkol Decaglyn 1-L), polyglyceryl-10 oleate (Nikkol Decaglyn 1-0), and polyglyceryl-10 mono, dioleate (Caprol® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also preferred surfactants.

Propylene Glycol Fatty Acid Esters

Esters of propylene glycol and fatty acids are suitable surfactants for use in embodiments of the present invention. In this surfactant class, preferred hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Sterol and Sterol Derivatives

Sterols and derivatives of sterols are suitable surfactants for use in embodiments of the present invention. Preferred derivatives include the polyethylene glycol derivatives. A preferred surfactant in this class is PEG-24 cholesterol ether (Solulan C-24).

Polyethylene Glycol Sorbitan Fatty Acid Esters

A variety of PEG-sorbitan fatty acid esters are available and are suitable for use as surfactants in embodiments of the present invention. Among the PEG-sorbitan fatty acid esters, preferred surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80).

Polyethylene Glycol Alkyl Ethers

Ethers of polyethylene glycol and alkyl alcohols are suitable surfactants for use in embodiments of the present invention. Preferred ethers include PEG-3 oleyl ether (Volpo 3) and PEG-4 lauryl ether (Brij 30).

Sugar and its Derivatives

Sugar derivatives are suitable surfactants for use in embodiments of the present invention. Preferred surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, and octyl-β-D-thioglucopyranoside.

Polyethylene Glycol Alkyl Phenols

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present invention.

Polyoxyethylene-Polyoxypropylene (POE-POP) Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is “poloxamer” (CAS 9003-11-6). These polymers have the formula: HO(C2H4O)a(C3H6O)b(C2H4O)aH where “a” and “b” denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Sorbitan Fatty Acid Esters

Sorbitan esters of fatty acids are suitable surfactants for use in embodiments of the present invention. Among these esters, preferred hydrophobic surfactants include sorbitan monolaurate (Arlacel 20), sorbitan monopalmitate (Span-40), sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants

Ionic surfactants, including cationic, anionic and zwitterionic surfactants, are suitable hydrophilic surfactants for use in embodiments of the present invention. Preferred ionic surfactants include quaternary ammonium salts, fatty acid salts and bile salts. Specifically, preferred ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. These quaternary ammonium salts are preferred additives. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Fat-Soluble Vitamins and Salts Thereof

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: Alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K-S(II). Folic acid is also of this type, and although it is water-soluble at physiological pH, it can be formulated in the free acid form. Other derivatives of fat-soluble vitamins useful in embodiments of the present invention may easily be obtained via well-known chemical reactions with hydrophilic molecules.

Water-Soluble Vitamins and their Amphiphilic Derivatives

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and Their Salts

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and their derivatives are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has solubility in unbuffered water of less than about 4% (40 mg/ml). These include cystine, tyrosine, tryptophan, leucine, isoleucine, phenylalanine, asparagine, aspartic acid, glutamic acid, and methionine.

Organic Acids and their Esters and Anhydrides

Examples are acetic acid and anhydride, benzoic acid and anhydride, acetylsalicylic acid, diflunisal, 2-hydroxyethyl salicylate, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methyl ethyl ketone, ethyl acetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water soluble and can effectively carry the drugs off the device into the vessel walls.

EXAMPLES

The invention is further described in the following examples, which do not limit the scope of the invention described in the claims.

Example 1: Aqueous Aerosol Formulation

An exemplary aqueous formulation of rapamycin was prepared using the following components.

| Component | Amount (g) | Mass Fraction (w/w) |
|---|---|---|
| rapamycin | 0.1 | 0.01% |
| ethanol | 250 | 25% |
| propylene glycol | 250 | 25% |

-continued

| Component | Amount (g) | Mass Fraction (w/w) |
|---|---|---|
| polysorbate 80 | 0.02 | 0.002% |
| water | 500 | 50% |
| Total | 1000 | |

Blending Procedure: in a 1000 ml amber volumetric flask, blend 250 propylene glycol with 250 ethanol until uniform. Then sequentially dissolve first 100 mg rapamycin then 20 mg polysorbate 80 in the propylene glycol and ethanol solution. Add water to bring the volumetric to 1000 ml and stir or sonicate until uniform and all the rapamycin is dissolved. Store at controlled temperature away from light.

Example 2: Dry Powder Formulation

Batch 06RP68.HQ00008 and 06RP68.HQ00009. These two formulations are each a blend of micronized drug (rapamycin) particles dispersed onto the surface of lactose carrier particles. The final composition of each batch comprises 1% (w/w) drug particles having a mean diameter of about 2.60 microns and 3.00 microns, respectively. Drug particles having a suitable size range are made by wet polishing (06RP68.HQ00008) or jet milling (06RP68.HQ00009), as described below. While this example used 1% (w/w) rapamycin, a range 0.5 to 20% is practicable. The carrier particles consist of a blend of two carriers, Respitose® SV003, present at 95.5% (w/w) and having particle sizes of about 30 to 100 microns (equivalent spherical diameter), and Respitose® LH300 (Lactohale 300) present at 5.5% (w/w) and having particle sizes less than 10 microns (equivalent spherical diameter). After blending, the blends were assayed to confirmed homogeneity and drug content of 1%.

To reduce drug particle agglomeration and aid in the aerosolization of drug particles several other excipients are optionally included. Optional excipients include phospholipids, such as dipalmitylphosphatidylcholine (DPPC) and lecithin, and metal fatty acid salts, such as magnesium stearate. These can be coated on the carrier particles in weight ratio of excipient to large carrier particle ranging from 0.01 to 0.5%.

Capsule Filling:

20 milligrams of the powder blends from Batch 06RP68.HQ00008 and Batch 06RP68.HQ00009 were loaded into size #3 HPMC capsules to produce drug product. For these blends it was feasible to load from 5 to 35 milligrams of drug into #3 size capsules and empty greater than 95% of the loaded blend from the capsule upon actuation in Plastiape® RS01 Model 7 or Plastiape® RS00 Model 8 devices at flow rates ranging from 60 to 100 liters per minute.

Example 3: Determination of Rapamycin in Lung and Blood Following Administration by Oropharyngeal Aspiration (OPA) and Oral Gavage to C57BL6 Mice This study was conducted to evaluate the concentration of rapamycin in male C57BL/6 mice after administration of rapamycin at a very high target dose of 1 mg/kg by gavage and oropharyngeal aspiration (OPA). A method for the analysis of rapamycin in mouse blood and lung homogenate was developed using liquid chromatography with tandem mass spectrometry detection (LC-MS/MS). Calibration curves of rapamycin using triplicate concentrations were analyzed between 1 ng/mL and 2000 ng/mL in mouse blood, and between 2 ng/mL and 20,000 ng/mL in mouse lung homogenate. Accuracy, precision and linearity were within expected ranges.

In pilot studies, the efficiency of vehicle delivery to the lungs via oropharyngeal aspiration with a volume of 50 μL per mouse was evaluated by administration of Evans Blue dye. The presence of blue dye only in lungs was verified visually, and the absence of blue dye in the stomach demonstrated that delivery to the stomach was avoided in the procedure used.

Rapamycin was administered to male C57BL/6 mice (N=6) by gavage at a dose of 1.0 mg/kg either orally or via OPA. The oral dose was formulated using pharmaceutical oral liquid formulation Rapamune Oral® (Pfizer). Rapamycin for OPA was prepared by dissolving the test article in an appropriate volume of ethanol, and then addition of an appropriate volume of water to prepare a 10% ethanol solution at a concentration of 1 mg rapamycin/mL. Rapamycin was administered to 2 groups of 6 male C57BL/6 mice by OPA under isoflurane anesthesia. An additional group of 6 mice received vehicle only (10% ethanol in water). At 1 h after administration a group of 6 mice receiving oral and OPA rapamycin were euthanized, and blood was obtained by cardiac puncture, and the lungs removed. The remaining mice in each group administered rapamycin or vehicle by OPA were observed for an additional 3 days. At the 72-h necropsy, blood was obtained by cardiac puncture and the lungs removed. No adverse effects were observed in rapamycin- or vehicle-treated mice in the 72 h period following dosing.

The concentration of rapamycin was determined in the collected blood and in lung homogenate by LC-MS/MS. At 1 h following OPA of rapamycin, the concentration of rapamycin was ~6 fold higher in lung tissue (3794±1259 ng/g tissue) than in blood (641±220 ng/ml). Following oral administration of a similar dose of rapamycin, the 1-h lung and blood concentrations of rapamycin were 71±43 ng/g and 23±16 ng/mL, respectively. Lung homogenate concentrations following OPA were 53-fold higher than those measured following oral administration of the same high dose (1 mg/kg) of rapamycin. The data suggests that delivery of lower doses of rapamycin to lung (dose levels that do not saturate system) will result in rapamycin levels in the lung that can be achieved by oral dosing but with significantly less rapamycin in the blood than occurs with oral dosing.

Materials and Methods

Test Substance:

Sirolimus (Rapamune, Rapamycin) MW 914.172, $C_{51}N_{79}NO_{12}$, CAS NUMBER: 53123-88-9. Source (for oral gavage): Rapamune Oral® (Pfizer) for oral administration, Lot No.: MWGT, Expiration: July 2016. Source (for OPA): Rapamycin (Sirolimus) solid, LC Laboratories, Woburn Mass., Lot No.: ASW-127, Expiration: December 2023.

Animals:

Male C57BL/6 mice, approximately 8 weeks of age, from Charles River Laboratories, Inc, Raleigh, N.C. Animals were fed Certified Purina Rodent Chow #5002 and were furnished tap water ad libitum. The analysis of each feed batch for nutrient levels and possible contaminants was performed by the supplier, examined by the Study Director, and maintained in the study records. The feed was stored at approximately 60-70° F., and the period of use did not exceed six months from the milling date. Mice were housed (one per cage) in polycarbonate cages with stainless steel bar lids accommodating a water bottle. Cage sizes are approximately 11.5"×7.5"×5" high (70 sq. in. floor space) for mice. Contact bedding was Sani-Chips hardwood chips (P. J. Murphy Forest Products Co.; Montville, N.J.). Mice were quarantined for a period of 5 days before use on a study. A veterinarian or qualified designee examined the animals prior to their release from quarantine. Temperature and relative humidity in RTI animal rooms were continuously monitored, controlled, and recorded using an automated system (Siebe/Barber-Colman Network 8000 System with Revision 4.4.1 for Signal® software [Siebe Environmental Controls (SEC)/Barber-Colman Company; Loves Park, Ill.]). The target environmental ranges were 64-79° F. (18° C.-26° C.) for temperature and 30-70% relative humidity, with a 12-h light cycle per day. At the end of the in-life phase, the mice were euthanized by overexposure to carbon dioxide.

Test Chemical Preparation: Evans Blue was prepared at 0.5% w/v in sterile distilled water. Rapamune Oral® was administered as supplied for oral dosing. Rapamycin (solid) was dissolved in ethanol and diluted with sterile distilled water to provide a final concentration of 0.5 mg/mL in 10% ethanol.

Dosing:

Each animal was weighed prior to dosing to determine the amount of dose to be administered. A single gavage dose was administered using a 100-μL glass syringe (Hamilton, Reno, Nev.) fitted with a ball-tipped 20-G stainless steel gavage dosing needle (Popper & Sons Inc., New Hyde Park, N.Y.). The dose administered to each animal was determined from the weight of the full syringe minus that of the empty syringe. The dosing time was recorded. Dosing of animals was spaced apart to allow blood collection at the appropriate times. The dose formulations administered to each group are shown below.

For oropharyngeal aspiration group animals, a single dose of rapamycin (50 μL) was administered to each mouse under isoflurane anesthesia, using a 100 μL glass syringe (Hamilton, Reno, Nev.) fitted with a ball-tipped 24-G stainless steel gavage dosing needle (Popper & Sons Inc., New Hyde Park, N.Y.). The mouse was weighed prior to dosing, and the dose of rapamycin administered was recorded by weight. Each mouse was anesthetized with isoflurane, and restrained with the mouth open. The tongue was held to one side of the mouth with forceps, and the dose was slowly injected into the distal part of the oral cavity. The nostrils were covered with a finger for two breaths to ensure aspiration (Rao et al., 2003).

TABLE 1

Study Design Summary

| Dose Group | Route | Compound | No. Animals | Target Dose (mg/ml) | Target Dose (ul) | Target Dose (mg/kg) | Collection Time | Samples Collected |
|---|---|---|---|---|---|---|---|---|
| 1 | OA | Evans Blue | 6 | — | 50 | 0 | 1 | blood, lung |
| 2 | OA | Rapamycin | 6 | 0.5 | 50 | 1.0 | 1 | blood, lung |
| 3 | Gavage | Rapamune Oral | 6 | 1.0 | 25 | 1.0 | 1 | blood, lung |
| 4 | OA | Vehicle | 6 | 0 | 50 | 1.0 | 72 | blood, lung |
| 5 | OA | Rapamycin | 6 | 0.5 | 50 | 1.0 | 72 | blood, lung |

Collection of Blood and Lung Samples: At study termination (1 or 72 h after dosing), mice were anesthetized by exposure to CO2, and blood was collected by cardiac puncture with dipotassium EDTA as anticoagulant. Lung tissue was excised and divided into the right and left lung. The left lung was used for analysis, and the right lung flash frozen in liquid nitrogen and stored at −70° C. for further analysis.

Analysis of Samples for Rapamycin by LC-MS/MS: An LC-MS/MS method for analysis of rapamycin in lung and blood was prepared based on the published method of Wu et al. (2012). The volumes of blood and lung homogenate were reduced substantially from the published method. Triamcinolone was used as internal standard.

Lung homogenate was prepared by homogenization of weighed lung samples with 2.8-mm ball bearings in a homogenizer with tissue+deionized water (1:3 w/v) in a SPEX SamplePrep 2010 Geno/Grinder.

The concentrations of standards were arranged so that each standard came from an alternate stock standard. A six-point calibration curve, each made in triplicate, was employed for analyte quantitation. A simple linear regression model with or without weighting was employed for curve fitting. The concentration range determined was from 1-2000 ng/mL in blood and 2-2000 ng/mL in lung homogenate.

The following method performance parameters were considered acceptable; the coefficient of determination, r2, of ≥0.98 for concentration-response relationship; an accuracy of ≤±15% (for concentrations above LOQ) or ≤±20% (for concentration at LOQ) of the nominal value. $r^2$ was greater than 0.999 in all analysis.

Thirty (30) μL of matrix, 30 μL of spiking solution (methanol for blanks and samples), 10 μL Internal standard solution (in MeOH) and 90 μL of MeOH were pipetted into microcentrifuge tubes, vortexed briefly, then centrifuged for 6 min at 10,000 RPM at ~4° C. Aliquots (90 μL) of supernatant were transferred to LC vial inserts, and then analyzed by LC-MS/MS (Table 2).

TABLE 2

LC-MS/MS Method

| | |
|---|---|
| Column | Waters Acquity UPLC HSS T3 1.8 μm, 2.1 × 50 mm with VanGuard 2.1 × 5 mm HSS T3 1.8 μm. |
| Mobile Phase A | 10 mM Ammonium Acetate in water, 0.1% acetic acid |

TABLE 2-continued

| LC-MS/MS Method | |
|---|---|
| Mobile Phase B | MeOH |
| Injection Vol | 2 ul |
| Flow Rate | 0.5 ml/min |
| Gradient | 70% A for 1 min, a linear gradient to 5% A from 1-3 min, held for 1 min, a linear gradient to 70% A from 4-5.1 min, and held at 70% until 6 min |
| Rapamycin MRM | 931.70→864.70 |
| Triamcinolone (IS MRM) | 395.30→357.20 |

Data Collection and Reporting:

Study data was collected and reported in the Debra™ system version 5.5.10.72 (Lablogic Systems Ltd., Sheffield, England). This includes data for animal body weights, dose administered, dose time, and sample collection times. Calculations of dose administered and sample collection times were reported with the Debra™ system.

Results

Figure 2:
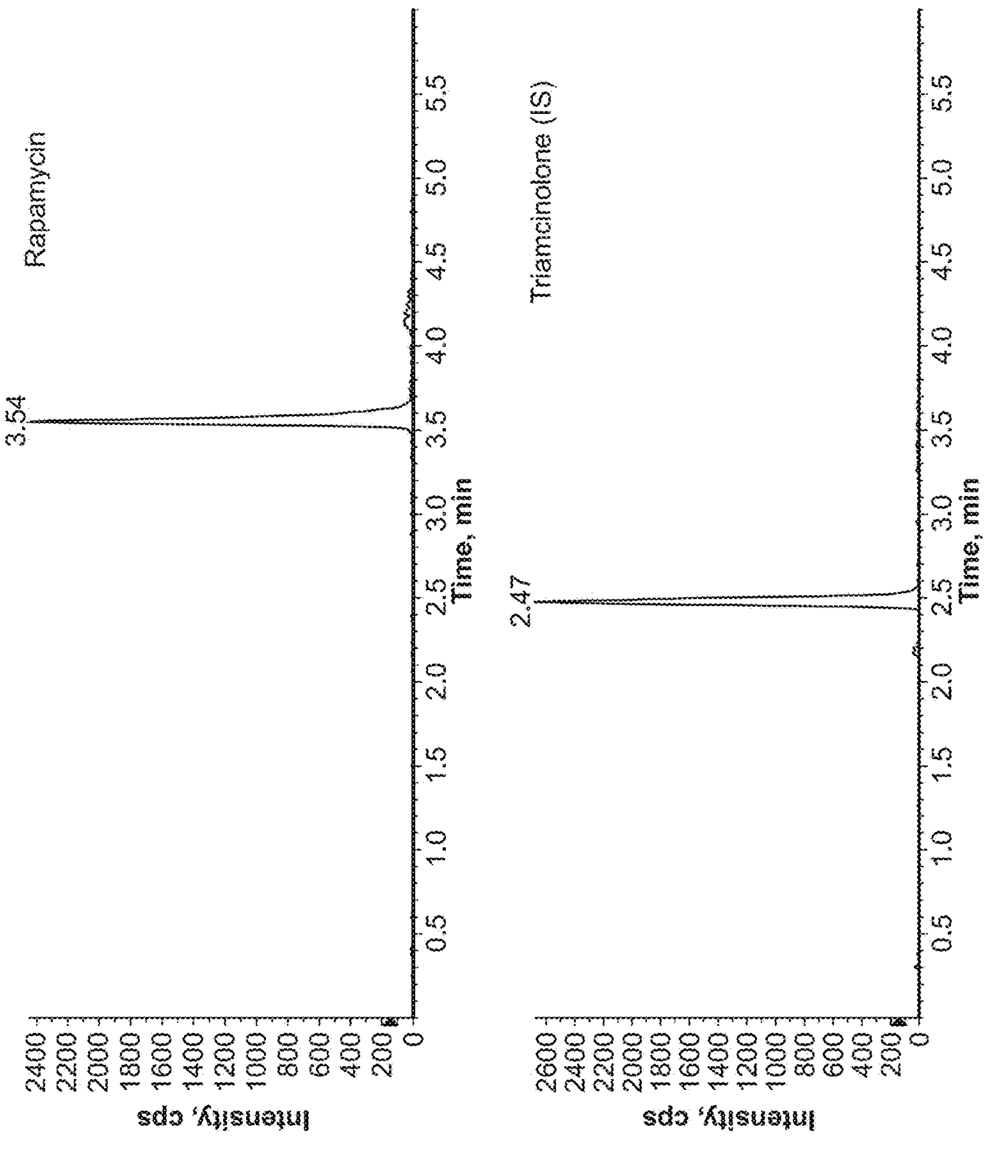
FIG. 2: Representative Chromatograms of 10.6 ng/mL Rapamycin (top) and Internal Standard (bottom) in Mouse Lung Homogenate.
Figure 3:
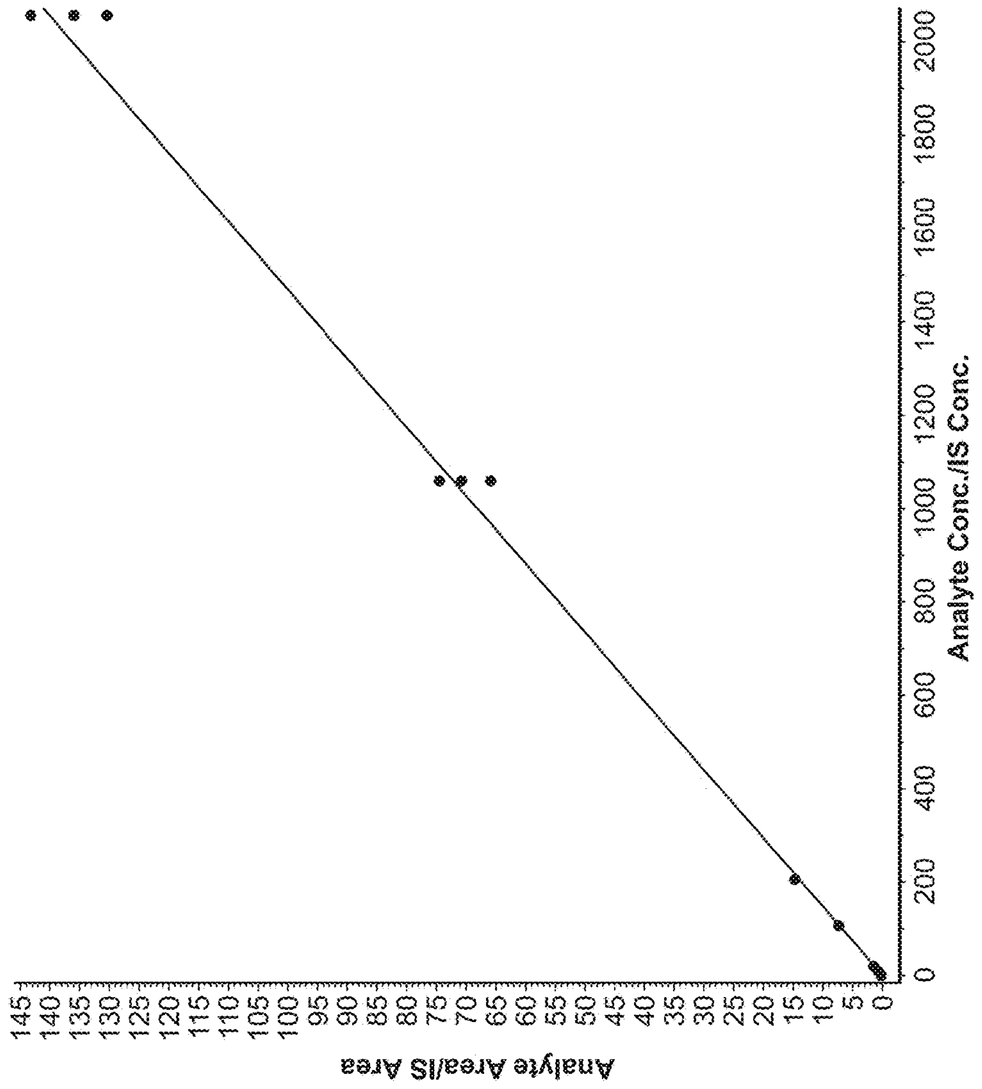
FIG. 3: Calibration Curve for Rapamycin in Mouse Blood.
Figure 4:
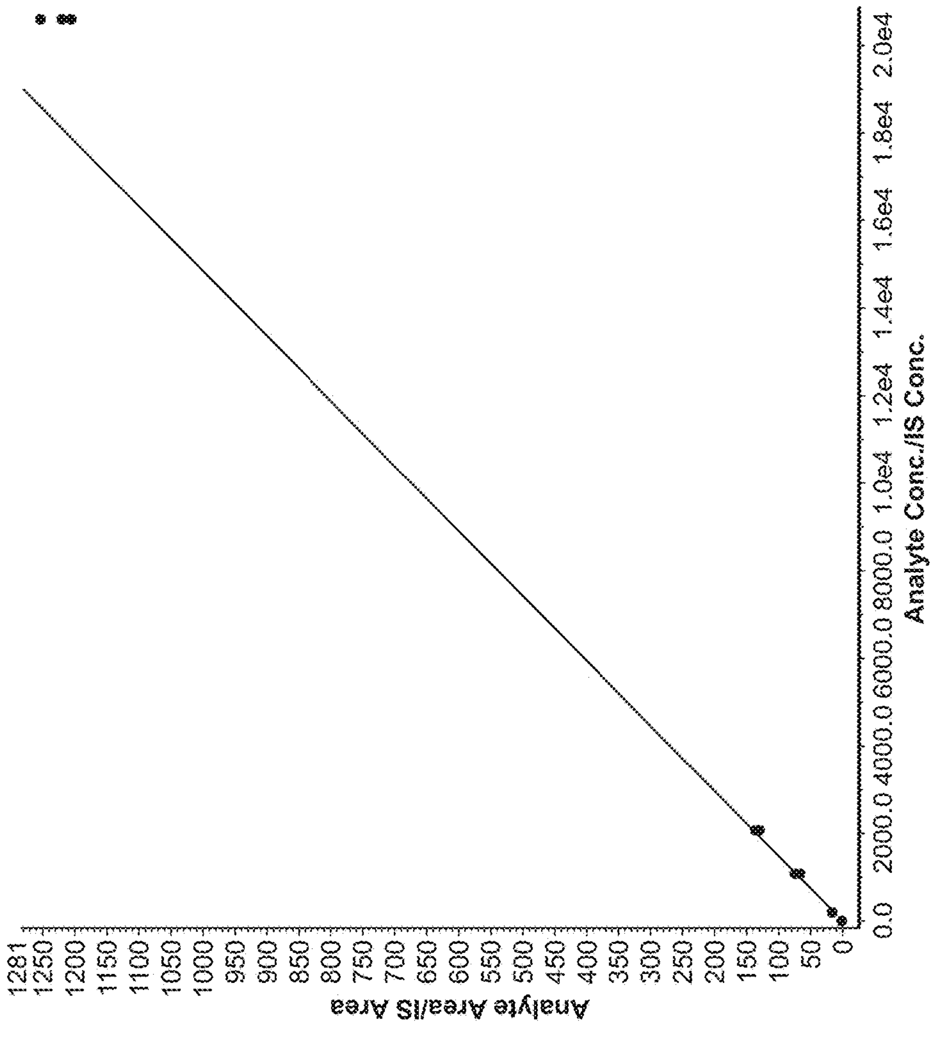
FIG. 4: Calibration Curve for Rapamycin in Mouse Lung Homogenate.
Figure 5:
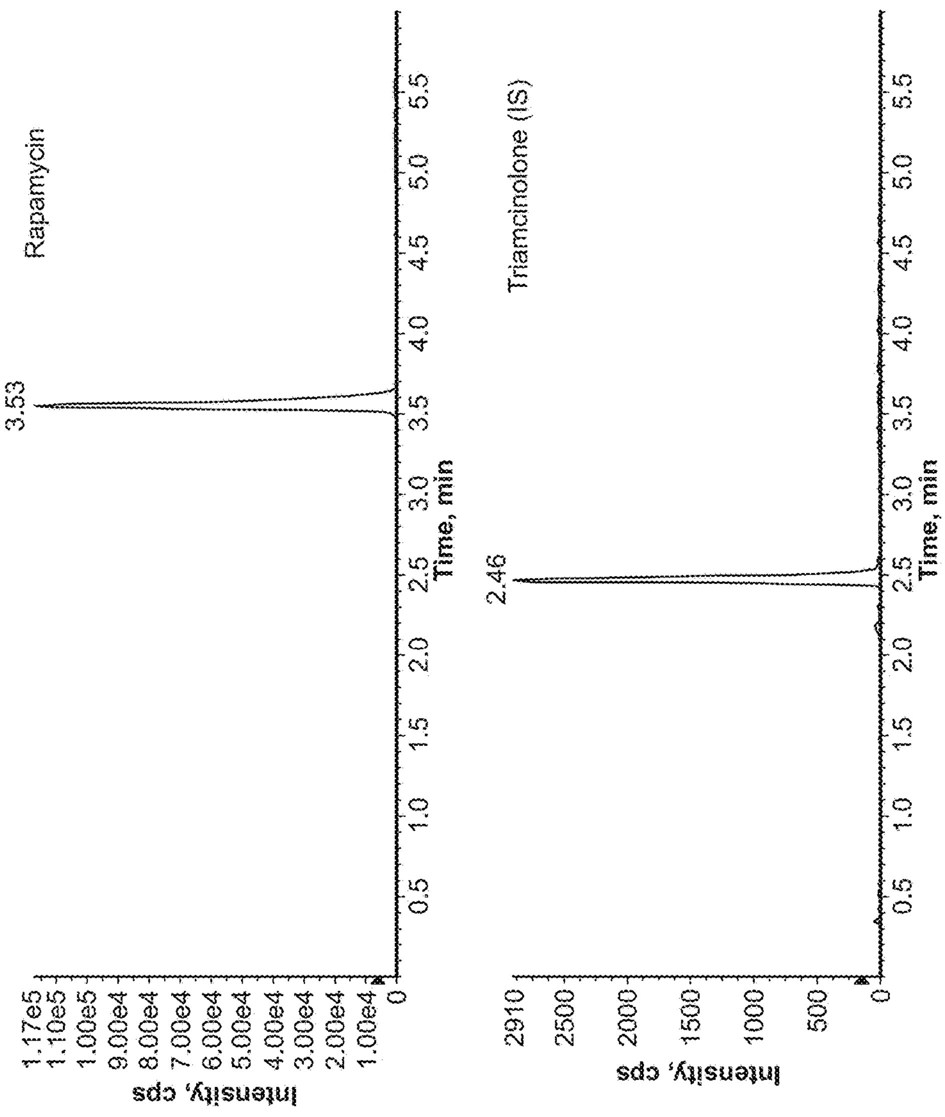
FIG. 5: Representative Chromatograms of Rapamycin (top) and Internal Standard (bottom) in Blood from Mouse 2-07 Administered Rapamycin by OPA.

Rapamycin Analysis:

The analysis of rapamycin was set up of sample volumes of 30 μL of blood and lung homogenate. Example chromatograms are shown for rapamycin and internal standard in blood and lung (FIGS. 1 and 2). Prior to the generation of study samples, triplicate calibration curves were generated for lung and blood, to verify method performance. The calibration range was from 1.0-2000 ng/mL for blood and 1-20,000 ng/mL for lung homogenate. Lung homogenate was prepared with 1 g of lung tissue homogenized in 3 volumes of water, to yield a 1:4 homogenate. Calibration curves are shown in FIGS. 3 and 4 for blood, lung homogenate, and solvent.

Oropharyngeal Aspiration:

Prior to the administration of rapamycin by oropharyngeal aspiration, administration of Evans Blue was used to verify that the OPA delivered the dose to the lungs. Mice were anaesthetized with isoflurane and administered Evans Blue by OPA, using a syringe equipped with a blunt needle. Immediately following OPA, the mice were euthanized and the lungs and stomach examined visually to ensure that the Evans Blue dye was delivered to the lungs, and was not delivered to the stomach. Four mice were successfully administered Evans Blue with all of the dye appearing to be located in the lungs and none in the stomach.

Rapamycin Administration:

The weight of dose solution administered was determined by weighing the charged syringe with dose solution prior to dosing, and weighing following dosing. The weight of dose solution administered was used to calculate the amount of rapamycin administered. The time of dosing was recorded as 0. Animals in groups 2 and 3 were euthanized at 1 h after dosing. Animals in groups 4 and 5 were observed for 72 h after dosing. No significant clinical signs were observed in any of the groups.

Figure 6:
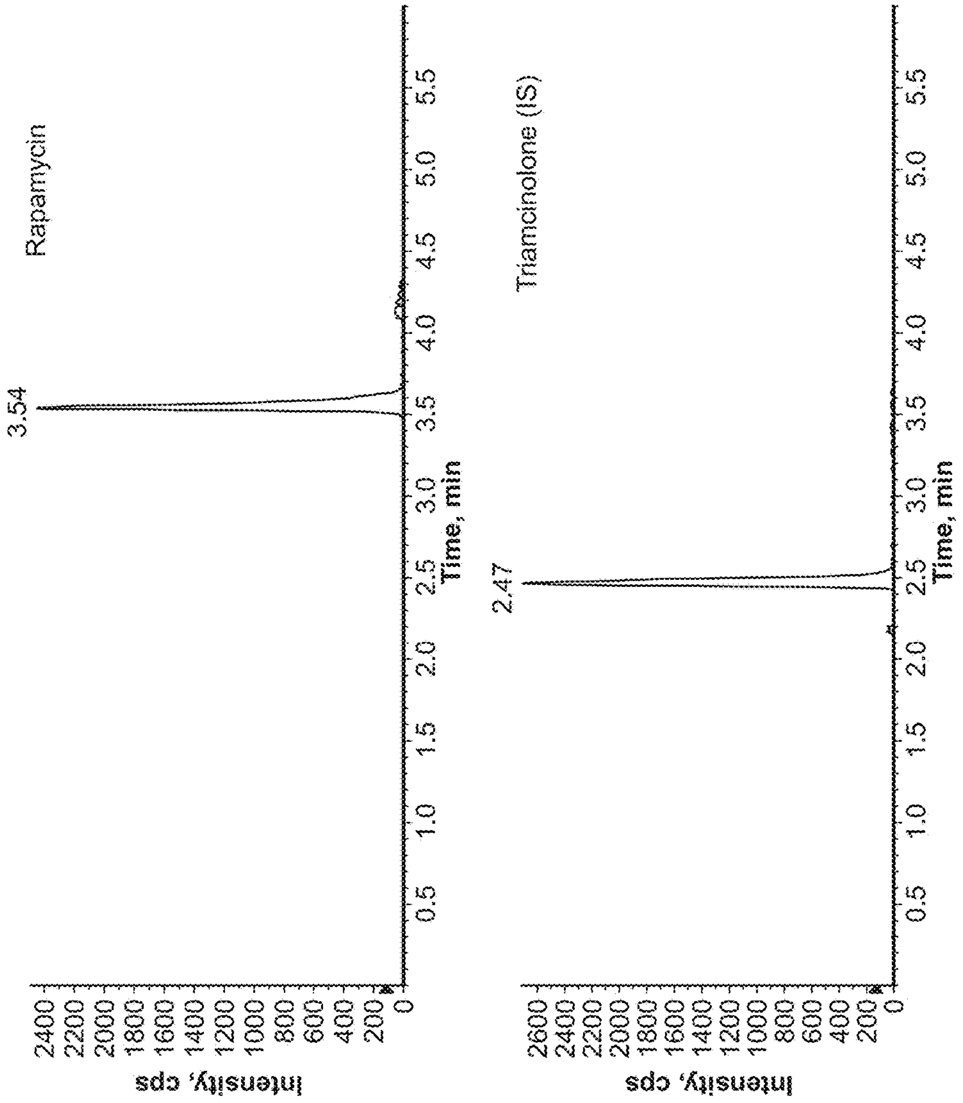
FIG. 6: Representative Chromatograms of Rapamycin (top) and Internal Standard (bottom) in Lung Homogenate from Mouse 2-07 Administered Rapamycin by OPA.
Figure 7:
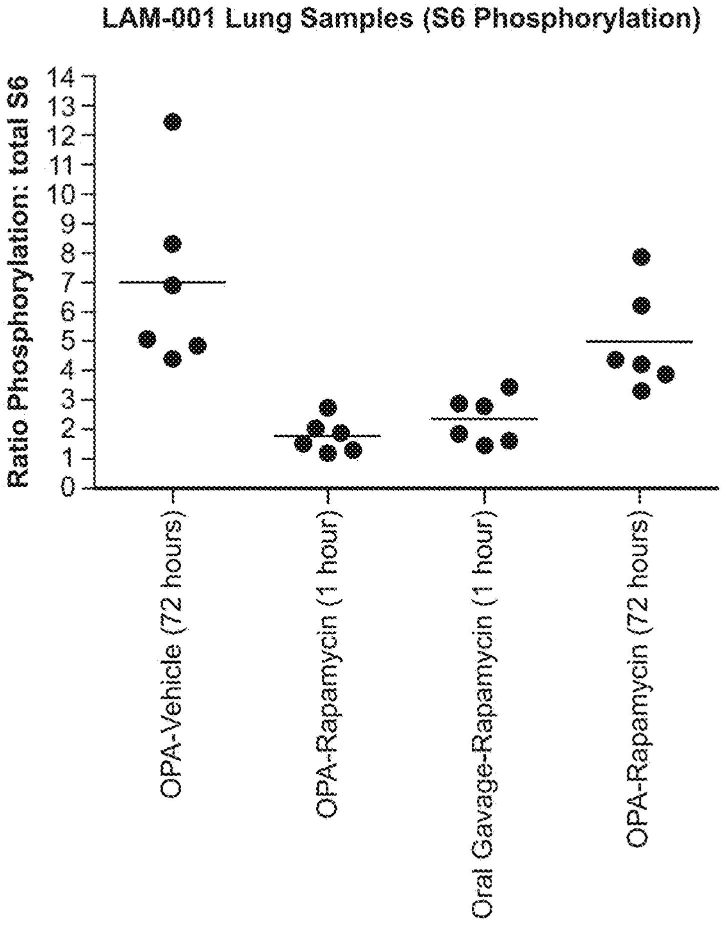
FIG. 7: S6 Phosphorylation in Mouse Lung Following OPA and oral administration of rapamycin.

Rapamycin Analysis in Blood and Lung:

Rapamycin was analyzed in mouse blood and left lung homogenate in all of the samples collected (FIGS. 6 and 7). Samples of the right lung from each animal were saved for potential further analysis. Summary data for the samples are provided in Table 3.

TABLE 3

Concentration of Rapamycin in Blood and Lung Following Oral and Oropharyngeal (OPA) Administration of Rapamycin to Mice (1 mg/kg)

| Animal No. | Route of Admin | Time post-dose (h) | Lung (ng/g tissue) | Blood (ng/ml) |
|---|---|---|---|---|
| 2-07 | OPA | 1 | 5040 | 615.5 |
| 2-08 | OPA | 1 | 2642 | 455.5 |
| 2-09 | OPA | 1 | 4500 | 622 |
| 2-10 | OPA | 1 | 1874 | 364.5 |
| 2-11 | OPA | 1 | 4006 | 937 |
| 2-12 | OPA | 1 | 4700 | 848.5 |
| Mean | | | 3794 | 641 |
| SD | | | 1259 | 220 |
| 3-13 | Gavage | 1 | 109.8 | 49.85 |
| 3-14 | Gavage | 1 | 24.66 | 11.3 |
| 3-15 | Gavage | 1 | 122.8 | 28.7 |
| 3-16 | Gavage | 1 | 54 | 28.35 |
| 3-17 | Gavage | 1 | <LOQ | 2.845 |
| 3-18 | Gavage | 1 | 43 | 19.35 |
| Mean | | | 71 | 23 |
| SD | | | 43 | 16 |
| 5-25 | OPA | 72 | 11.7 | <ELOQ |
| 5-26 | OPA | 72 | 11.4 | <ELOQ |
| 5-27 | OPA | 72 | 15.7 | <ELOQ |
| 5-28 | OPA | 72 | 10.8 | <ELOQ |
| 5-29 | OPA | 72 | 11.9 | <ELOQ |
| 5-30 | OPA | 72 | 13.6 | <ELOQ |
| Mean | | | 12.5 | |
| SD | | | 1.9 | |

For all sample sets, a triplicate calibration curve was analyzed with the sequence of standard set, sample replicate 1, standard set, sample replicate sample 2, standard set. At 1 h following OPA of rapamycin, the concentration of rapamycin was ~6 fold higher in lung tissue (3794±1259 ng/g tissue) than in blood (641±220 ng/ml). Following oral administration of a similar dose of rapamycin, the 1-h lung and blood concentrations of rapamycin were 71±43 ng/g and 23±16 ng/mL, respectively. Lung homogenate concentrations following OPA were 53-fold higher than those measured following oral administration of same high dose (1 mg/kg) of rapamycin.

Discussion

This study investigated the concentration of rapamycin in blood and lung tissue following administration of rapamycin by gavage in a commercial oral formulation, and by oropharyngeal administration (OPA) as a suspension prepared in 10% aqueous ethanol. No adverse effects were observed in rapamycin- or vehicle-treated mice up to 72 h following dosing via OPA. Prior to administration of rapamycin, an analytical method was developed, and the administration of a dye into the lung by OPA was verified. The concentrations of rapamycin in lung following OPA were 6-fold higher than in blood. At 72 h after OPA, rapamycin was below the limit of quantitation in blood, but was detectable in lung. This study indicated that rapamycin is available systemically following pulmonary administration, and that lung tissue concentrations greatly exceed that of blood at early and late time points following delivery to the lung.

These results further demonstrate that rapamycin delivered directly to the lung achieves an unexpectedly high local concentration of drug in lung tissue compared to the blood. This result was entirely unexpected from what is known about the pharmacology of rapamycin, which predicts an approximately equal concentration of the drug in lung tissue and the blood because rapamycin is known to distribute evenly throughout bodily tissues and should be cleared rapidly from the lung due to its high lipophilicity. Accordingly, these results indicate that direct administration of rapamycin to the lungs should be able to achieve a high enough delivered dose for therapeutic efficacy while at the same time achieving almost undetectable systemic availability, thereby eliminating the toxicities associated with oral administration that are due to systemic exposure to the drug. While toxicity to the lung itself is also of concern in view of earlier studies, the results here further unexpectedly indicate that relatively high amounts of rapamycin were not acutely toxic to lung tissue.

REFERENCES

Crowe, A., Bruelisauer, A. & Duerr, L. (1999). Absorption and intestinal metabolism of SDZ-RAD and rapamycin in rats. Drug Metabolism and Disposition, 27, 627-632.

Rao, G. V. S., Tinkle, S., Weissman, D. N., Antonini, J. M., Kashon, M. L., Salmen, R., Hubbs, A. F. (2003). Efficacy of a technique for exposing the mouse lung to particles aspirated from the pharynx. Journal of Toxicology and Environmental Health. Part A, 66(15), 1441-52. doi: 10.1080/15287390306417.

Wu, K., Cohen, E. E. W., House, L. K., Ramirez, J., Zhang, W., Ratain, M. J., & Bies, R. R. (2012). Nonlinear population pharmacokinetics of sirolimus in patients with advanced cancer. CPT: Pharmacometrics & Systems Pharmacology, 1 (October), e17. doi:10.1038/psp.2012.18.

Example 4: S6 Phosphorylation in Mouse Lung Following Oral and OPA Administration of Rapamycin As discussed above, our experiments showing the tissue distribution of rapamycin in lung and blood following oral administration and OPA demonstrated that direct administration of rapamycin to the lungs should be able to achieve a high enough delivered dose for therapeutic efficacy while at the same time achieving very low systemic exposure to the drug, thereby simultaneously improving therapeutic efficacy and eliminating many of the toxicities associated with oral administration of rapamycin. To validate this approach, we used the presence of phosphorylated S6 protein in murine lung tissue as a biomarker for mTOR activity. In the mouse strain used (C57bl/6), the mouse airway and alveolar epithelial cells have constitutively active (phosphorylated, "p") S6 protein. The S6 protein is typically phosphorylated by S6K which is downstream of mTORC1 and is activated, for example, downstream of growth factors such as epidermal growth factor (EGF), AKT, ERK, and RSK. mTORC1 promotes cell growth and proliferation by stimulating anabolic processes such as biosynthesis of lipids, proteins, and organelles, and suppressing catabolic processes such as autophagy. The mTORC1 pathway senses and integrates intracellular and extracellular signals, including growth factors, oxygen, amino acids, and energy status, in order to regulate a wide range of processes, such as protein and lipid synthesis and autophagy. mTORC1 is acutely sensitive to rapamycin.

In the present study, lung tissue was taken from the C57bl/6 mice treated as discussed above, either with vehicle (n=6), or 1 mg/kg rapamycin administered via OPA (n=6) or via oral gavage (n=6) at two time points post dosing, 1 hr and 72 hours. As discussed above, following OPA at 1 hr, rapamycin was detected at 641 ng/ml in the blood and 3794 ng/g tissue in the lung, and at 72 hrs was still detectable in the lung at 12.5 ng/g while being undetectable in the blood at that time point. Conversely, following oral (gavage) administration, at 1 hr, rapamycin was detected at 23 ng/ml in the blood and 71 ng/g tissue in the lung, and at 72 hrs was undetectable in either the lung or blood. As shown by the data in FIGS. 1 and 2, the level of phosphorylated S6 (pS6) was reduced substantially by both OPA and orally administered rapamycin at 1 hr and remained suppressed at 72 hr for OPA. pS6 was highest in the vehicle control because these mice have constitutively active mTOR signaling. These data show that a delivered dose of rapamycin sufficient to achieve about 70 ng/g drug in the lung substantially abrogates mTOR signaling in the lung tissue as measured by pS6 protein and that mTOR signaling remains suppressed at levels as low as 12.5 ng/g. These results validate our approach to utilize inhaled rapamycin for the treatment of diseases and disorders such as LAM, which is characterized by aberrantly high mTOR pathway activity by demonstrating that inhaled rapamycin can be delivered at much lower doses than orally administered rapamycin to simultaneously achieve high therapeutic efficacy and very low toxicity.

Example 5: Size Reduction of Rapamycin for Inhalable Compositions

Particle size of rapamycin was reduced to a target range of 2.0 μm<Dv50<3.0 μm using either a wet polishing or jet milling process. For jet milling, a lab scale MCOne unit from Jetpharma was used with the following operating conditions: venturi pressure 2-4 bar, milling pressure 3-5 bar, feed rate 90 g/h. For wet polishing, feed suspensions were prepared using purified water. A microfluidics high pressure homogenizer was used for the size reduction step and the resulting suspension was spray-dried. Details of the wet polishing process are set forth below.

The high pressure homogenizer used for the size reduction step of the wet polishing process was a pilot-scale Microfluidics High Pressure Homogenizer equipped with an auxiliary processing module (200 micron) and a 100 micron interaction chamber was used. The unit was operated at ~455 bar (~30 bar in the intensifier module hydraulic pressure). After microfluidization the fluid was removed by spray drying to generate a dry powder. A laboratory scale spray dryer, SD45 (BÜCHI, model B-290 Advanced) was equipped with a two fluid nozzle (cap and diameter were 1.4 and 0.7 mm, respectively). Two cyclones in series were used (being the first the standard Buchi cyclone and the second the high-performance Buchi cyclone) to collect the dried product. The spray drying unit was operated with nitrogen and in single pass mode, i.e. without recirculation of the drying nitrogen. The aspirator, blowing nitrogen, was set at 100% of its capacity (flow rate at maximum capacity is approximately 40 kg/h). The flow rate of the atomization nitrogen was adjusted to a value in the rotameter of 40±5 mm. Before feeding the product suspension, the spray dryer was stabilized with purified water, during which the flow rate was adjusted to 6 ml/min (20% in the peristaltic pump). The inlet temperature was adjusted to achieve the target outlet temperature (45° C.). After stabilization of the temperatures, the feed of the spray dryer was commuted from purified water to the product suspension (keeping the same flow rate used during stabilization) and the inlet temperature once again adjusted in order to achieve the target outlet temperature. At the end of the stock suspension, the feed was once more commuted to purified water in order to rinse the feed line and perform a controlled shut down. The dry product in the collection flasks under both cyclones was weighed and the yield calculated as the mass percentage of the dry product in relation to the total solids in the suspension fed to the high pressure homogenizer.

Particle size distribution was analyzed by laser diffraction. Solid state characterization (for polymorphic form and purity) was performed by high pressure liquid chromatography (HPLC), X-ray powder diffraction (XRPD), and differential scanning calorimetry (mDSC). Water content was determined by the Karl Fischer method.

Jet milling produced crystalline rapamycin powder with a monodisperse particle size distribution having Dv10 of 1.5 microns, a Dv50 of 2.7 microns and a Dv 90 of 4.9 microns, as shown in Table 4 below.

Wet polishing produced crystalline rapamycin powder with a monodisperse particle size distribution having a Dv10 of 1.0 microns, a Dv50 of 2.4 microns and a Dv 90 of 5.0 microns (Table 5).

Both methods produced particles of rapamycin within the target range and neither process showed an impact on polymorphic form or purity of the rapamycin. The tables below show in-process control data for the jet milling and wet polishing processes. The data indicate that both processes were able to produce API particle sizes within the target range without impacting API purity or polymorphic form.

TABLE 4

| Jet Milling Data | | | | |
|---|---|---|---|---|
| PSD | μm | Dv10 | Dv50 | Dv90 |
| | | 1.51 | 2.74 | 4.91 |
| XRPD | — | Similar to API (sirolimus) diffractogram | | |
| mDSC | (T_onset, ° C.) | | 182.2 | |
| KF | % w/w | | 0.30 | |
| HPLC | Assay (% w/w) | | 99.5 | |
| (% area) | Sirolimus | | 99.35 | |

TABLE 5

| Wet Polishing Data | | | | |
|---|---|---|---|---|
| PSD | μm | Dv10 | Dv50 | Dv90 |
| | | 1.05 | 2.42 | 4.97 |
| XRPD | — | Similar to API (sirolimus) diffractogram | | |
| mDSC | (T_onset, ° C.) | | 185.7 | |
| KF | % w/w | | 0.30 | |
| HPLC | Assay (% w/w) | | 99.0 | |
| (% area) | Sirolimus | | 99.42 | |

Example 6: Aerosol Performance Testing of Dry Powder Compositions

The capsules produced in the example above were placed into the device indicated in the tables below and actuated. The aerosol performance delivered from the devices/capsules containing blends from Batch 06RP68.HQ00008 and Batch 06RP68.HQ00009 were characterized using a next generation impactor (NGI) according to the methods described in Chapters 905 and 601 of the USP. The aerosols were tested at flow rates of 60 and 100 liters per minute (LPM). The fine particle dose (FPD) and fine particle fraction (FPF) are shown in the tables below. Mass median aerodynamic diameters (MMAD) and geometric standard deviations (GSD) are also shown.

TABLE 6

| 06RP68.HQ00008 (Wet Polished) + Plasitape RS01 Model 7 | | | | |
|---|---|---|---|---|
| | 60 LPM | | 100 LPM | |
| | Mean | % RSD | Mean | % RSD |
| FPD (μg) | 57.31 | 2.37 | 67.21 | 12.46 |
| FPF (%) | 39.49 | 1.85 | 44.12 | 8.99 |
| MMAD (μm) | 2.81 | 2.22 | 2.49 | 11.97 |
| GSD | 2.02 | 0.99 | 2.19 | 8.25 |

TABLE 7

| 06RP68.HQ00008 (Wet Polished) + Plastiape RS00 Model 8 | | | | |
|---|---|---|---|---|
| | 60 LPM | | 100 LPM | |
| | Mean | % RSD | Mean | % RSD |
| FPD (μg) | 58.40 | 0.98 | 62.39 | 6.35 |
| FPF (%) | 39.68 | 1.68 | 41.34 | 3.70 |
| MMAD (μm) | 2.63 | 7.28 | 2.58 | 6.00 |
| GSD | 2.05 | 3.69 | 2.15 | 6.32 |

TABLE 8

| 06RP68.HQ00009 (Jet Milled) + Plastiape RS01 Model 7 | | | | |
|---|---|---|---|---|
| | 60 LPM | | 100 LPM | |
| | Mean | % RSD | Mean | % RSD |
| FPD (μg) | 52.33 | 6.72 | 58.51 | 15.84 |
| FPF (%) | 33.73 | 3.91 | 36.69 | 9.86 |
| MMAD (μm) | 3.32 | 2.27 | 3.02 | 4.14 |
| GSD | 2.05 | 1.02 | 2.24 | 1.79 |

TABLE 9

| 06RP68.HQ00009 (Jet Milled) + Plastiape RS00 Model 8 | | | | |
|---|---|---|---|---|
| | 60 LPM | | 100 LPM | |
| | Mean | % RSD | Mean | % RSD |
| FPD (μg) | 52.56 | 2.02 | 59.11 | 4.74 |
| FPF (%) | 33.97 | 0.86 | 36.01 | 4.20 |
| MMAD (μm) | 3.06 | 1.91 | 2.93 | 0.98 |
| GSD | 2.04 | 0.98 | 2.21 | 2.73 |

Based on these aerosol performance data, the wet polished drug particles are preferred. They resulted in a higher fine particle dose, higher fine particle fraction, a particle size distribution that would exhibit penetration into both the central and peripheral lung regions, and would have less oral deposition.

Example 7: Pharmacokinetic Modeling of Rapamycin

Based on the aerosol performance 06RP68.HQ00008 (Wet Polished)+Plasitape RS01 Model as shown above, and the results of animal experiments in Example 3, it can be expected that delivery of inhaled rapamycin directly to the lung in humans will similarly result in persistent lung concentrations that are sufficiently high to be therapeutically effective, but with low systemic exposure (low blood concentrations) thereby effectively minimizing side effects due to systemic exposure. A two compartment, pharmacokinetic model was developed to predict the concentrations in the blood and lungs in humans after repeat QD dosing using the formulation and DPI inhaler in Table 6. For the pharmacokinetic model, human PK parameters from the Rapamune® (NDA 21-110, and NDA 21-083) summary basis of approval were used: the volume of distribution was assumed to be 780 liters, clearance was 0.0003/minute, and elimination half-life was 42.3 hours (assuming equivalency to rapamycin IV dosing). Absorption half-life of rapamycin from the lung was estimated to be approximately 0.5 hours, similar to other highly lipophilic compounds, such as fluticasone proprionate for which lung absorption data is available. Bioavailability of rapamycin depositing in the lung was assumed to be approximately 100%. Bioavailability of rapamycin absorbed by the GI route through oropharyngeal deposition or removal from the upper airways by mucociliary clearance was assumed to be 14% as reported in the Rapamune® summary basis for approval. For a typical human inspiratory maneuver at a flow rate of 60 liters per minute, as shown in Table 6, the fine particle dose was 57 micrograms, and the fine particle fraction was 40%.

Figure 8:
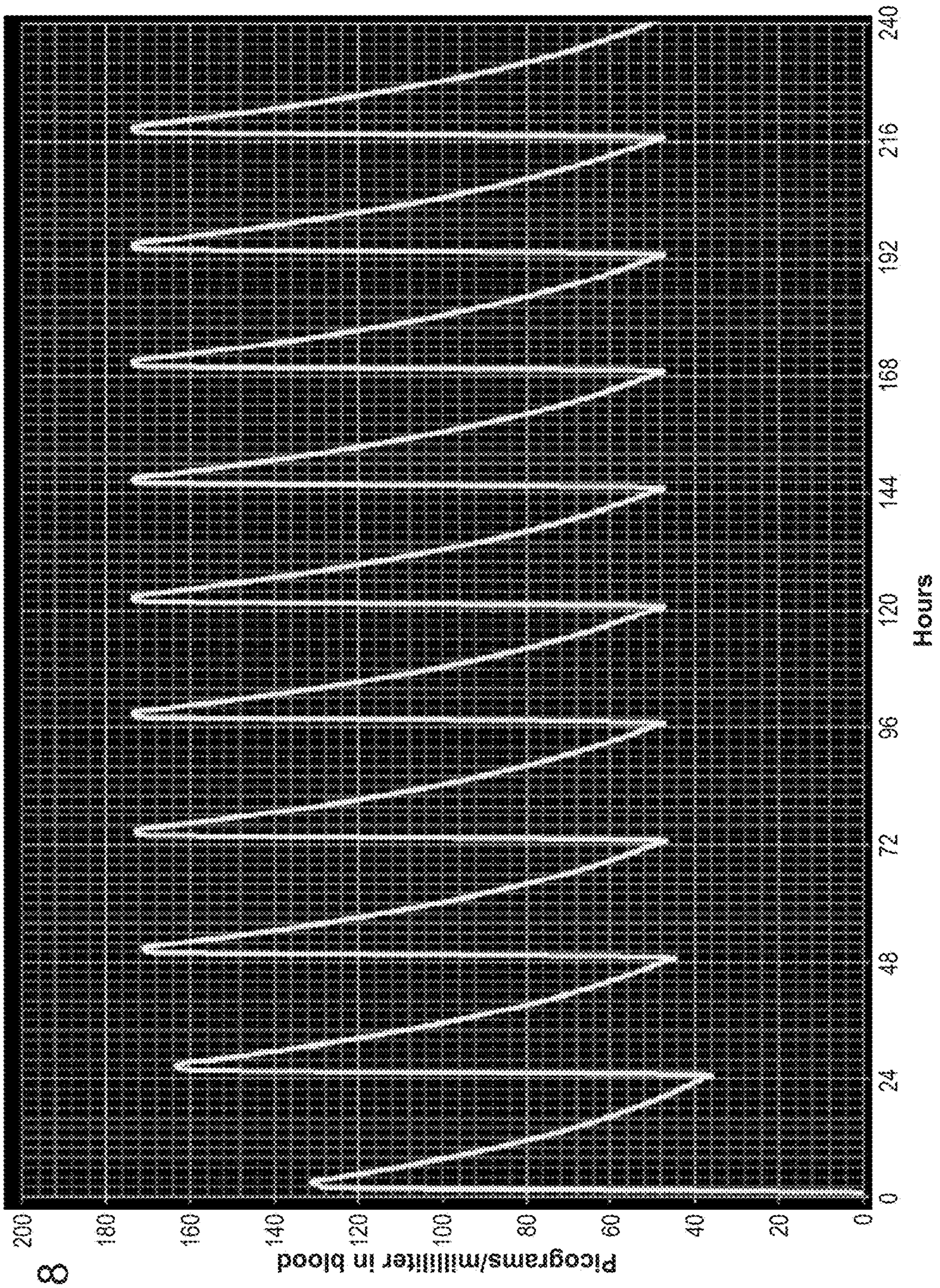
FIG. 8: Predicted rapamycin blood concentrations for pulmonary administration repeated once daily.

The model predicts achieving an average steady state concentration after 11 days as shown in FIG. 8. From the figure it can be seen that once daily repeat dosing of 57 micrograms delivered to the lungs results in trough blood concentrations of approximately 50 picograms/ml, and maximum concentrations below 200 picograms/ml, substantially below the concentrations of 5-15 ng/ml reported in McCormack et al. (2011), "Efficacy and safety of sirolimus in lymphangioleiomyomatosis", *N Engl J Med* 364:1595-1606. Assuming a lung tissue mass of 850 grams, no metabolism in the lung and a lung absorption half life or 30 minutes, 57 micrograms rapamycin delivered to the lungs would result in therapeutic levels in the lung tissue, with local lung concentrations of rapamycin as high as approximately 14 ng/gram.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating Lymphangioleiomyomatosis in a human subject in need of such treatment, the method comprising administering to the subject by inhalation a pharmaceutical dry powder composition comprising microparticles of sirolimus, particles of a carrier, and one or more optional excipients, wherein the microparticles of sirolimus have a mean diameter of from 1 to 5 microns, and wherein the sirolimus is the only therapeutic agent in the composition.

2. The method of claim 1, wherein the carrier is selected from the group consisting of arabinose, glucose, fructose, ribose, mannose, sucrose, trehalose, lactose, maltose, starches, dextran, mannitol, lysine, leucine, isoleucine, dipalmitylphosphatidylcholine, lecithin, polylactic acid, poly (lactic-co-glutamic) acid, and xylitol, or mixtures of any of the foregoing.

3. The method of claim 1, wherein the administration achieves a respirable dose of from 5 to 500 micrograms of sirolimus is delivered to the lung.

4. The method of claim 1, wherein the administration is once daily.

5. The method of claim 1, wherein the administration achieves a blood trough level of sirolimus of less than 2 ng/ml 12 or 24 hours after administration.

6. The method of claim 1, wherein the amount of sirolimus in the pharmaceutical dry powder composition is from 10 to 250 micrograms.

7. The method of claim 1, wherein the amount of sirolimus in the pharmaceutical dry powder composition is from 20 to 100 micrograms.

* * * * *